(12) United States Patent
Reddy et al.

(10) Patent No.: US 9,006,448 B2
(45) Date of Patent: Apr. 14, 2015

(54) PROCESS FOR THE PREPARATION OF BENZIMIDAZOLE DERIVATIVES AND ITS SALTS

(75) Inventors: Manne Satyanarayana Reddy, Hyderabad (IN); Chakilam Nagaraju, Hyderabad (IN); Srinivasan Thirumalai Rajan, Hyderabad (IN); Sajja Eswaraiah, Hyderabad (IN); Achampeta Kodanda Ramprasad, Hyderabad (IN); Suraparaju Raghuram, Hyderabad (IN)

(73) Assignee: MSN Laboratories Private Limited, Medak District, Telangana (IN)

( * ) Notice: Subject to any disclaimer, the term of this patent is extended or adjusted under 35 U.S.C. 154(b) by 0 days.

(21) Appl. No.: 13/995,786

(22) PCT Filed: Dec. 7, 2011

(86) PCT No.: PCT/IN2011/000836
§ 371 (c)(1),
(2), (4) Date: Jun. 19, 2013

(87) PCT Pub. No.: WO2012/077136
PCT Pub. Date: Jun. 14, 2012

(65) Prior Publication Data
US 2014/0148601 A1    May 29, 2014

(30) Foreign Application Priority Data

Dec. 6, 2010 (IN) ............................ 3670/CHE/2010
May 27, 2011 (IN) ............................ 1801/CHE/2011
Sep. 21, 2011 (IN) ............................ 3261/CHE/2011

(51) Int. Cl.
*C07D 401/12* (2006.01)
*C07D 233/56* (2006.01)

(52) U.S. Cl.
CPC ............ *C07D 401/12* (2013.01); *C07D 233/56* (2013.01)

(58) Field of Classification Search
CPC ...................................................... C07D 401/12
USPC ........................................................ 546/273.4
See application file for complete search history.

(56) References Cited

U.S. PATENT DOCUMENTS

| 2005/0234104 A1 | 10/2005 | Schmid et al. |
| 2010/0210845 A1 | 8/2010 | Zerban et al. |

FOREIGN PATENT DOCUMENTS

| CN | 102050814 | 5/2011 |
| WO | WO 98/37075 | 8/1998 |
| WO | WO 2005/028468 A1 | 3/2005 |
| WO | WO 2006/000353 A1 | 1/2006 |
| WO | WO 2007/071742 A1 | 6/2007 |
| WO | WO 2008/043759 A1 | 4/2008 |
| WO | WO 2008/095928 A1 | 8/2008 |
| WO | WO 2009/111997 A1 | 9/2009 |
| WO | WO 2009/153215 A1 | 12/2009 |
| WO | WO 2010/045900 A1 | 4/2010 |
| WO | WO 2011/061080 A1 | 5/2011 |
| WO | WO 2011/110478 A1 | 9/2011 |
| WO | WO 2011/110876 A1 | 9/2011 |

OTHER PUBLICATIONS

International Search Report for International Application No. PCT/IN2011/00836, "Process for the Preparation of Benzimidazole Derivatives and Its Salts" Date of mailing: Jul. 12, 2012.

Written Opinion of the International Searching Authority for International Application No. PCT/IN2011/00836, "Process for the Preparation of Benzimidazole Derivatives and Its Salts", Date of mailing: Jul. 12, 2012.

Notification Concerning Transmittal of International Preliminary Report on Patentability for International Application No. PCT/IN2011/00836, "Process for the Preparation of Benzimidazole Derivatives and Its Salts" Date of Issuance: Jun. 12, 2013.

*Primary Examiner* — Patricia L Morris
(74) *Attorney, Agent, or Firm* — Hamilton, Brook, Smith & Reynolds, P.C.

(57) ABSTRACT

An dabigatran etexilate intermediate of Formula-6a, and the use in the preparation of dabigatran etexilate thereof.

16 Claims, 4 Drawing Sheets

PROCESS FOR THE PREPARATION OF BENZIMIDAZOLE DERIVATIVES AND ITS SALTS

RELATED APPLICATION

This application is the U.S. National Stage of International Application No. PCT/IN2011/000836, filed Dec. 7, 2011, which designates the U.S., published in English, and claims priority under 35 U.S.C. 119 or 365(c) to Indian patent application No. 3670/CHE/2010, filed Dec. 6, 2010, Indian patent application No. 1801/CHE/2011, filed May 27, 2011 and Indian patent application No. 3261/CHE/2011, filed Sep. 21, 2011. The entire teachings of the above applications are incorporated herein by reference.

FIELD OF INVENTION

The present invention relates to an improved process for the preparation of 1-methyl-2-[N-[4-(N-n-hexyloxycarbonylamidino)phenyl]aminomethyl]benzimidazol-5-yl-carboxylicacid-N-(2-pyridyl)-N-(2-ethoxycarbonylethyl)amide compound of formula-1 and its methanesulfonate salt compound of formula-1a, represented by the following structural formulas:

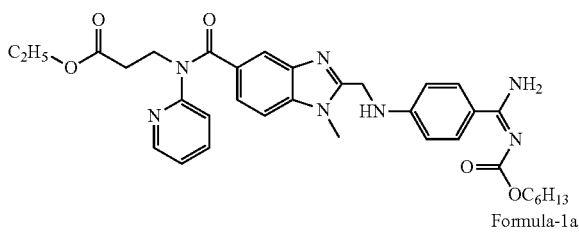

Further, the present invention also provides novel acid addition salts of 1-methyl-2-[N-[4-amidinophenyl]aminomethyl]benzimidazol-5-yl-carboxylicacid-N-(2-pyridyl)-N-(2-ethoxycarbonylethyl)amide, preferably oxalate salt, represented by the structural formula-6a, an useful intermediate in the synthesis of highly pure compound of formula-1a.

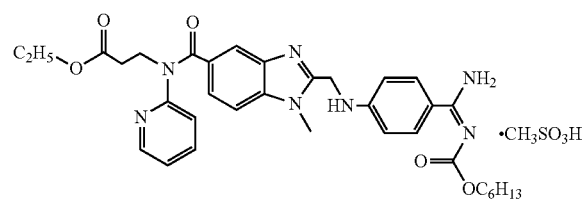

Further, the present invention provides a method for purification of compound of formula-5 and formula-1a.

The 1-methyl-2-[N-[4-(N-n-hexyloxycarbonylamidino)phenyl]aminomethyl]benzimidazol-5-yl-carboxylicacid-N-(2-pyridyl)-N-(2-ethoxycarbonylethyl)amide methanesulfonate is commonly known as Dabigatran etexilate mesylate.

Dabigatran is an anticoagulant drug selected from the class of the direct thrombin inhibitors developed by Boehringer Ingelheim and is used for the treatment of thrombosis, cardiovascular diseases and the like. Dabigatran etexilalte mesylate was approved by both in US and Europe and commercially available under the brand name of Pradaxa.

BACKGROUND OF THE INVENTION

Dabigatran etexilate and process for its preparation was first disclosed in WO 98/37075. The disclosed process involves the reaction of 1-methyl-2-[N-[4-amidinophenyl]aminomethyl]benzimidazol-5-yl-carboxylicacid-N-(2-pyridyl)-N-(2-ethoxycarbonylethyl)amide hydrochloride (herein after referred as dabigatran hydrochloride) with hexylchloroformate in presence of potassium carbonate in tetrahydrofuran/water provides 1-methyl-2-[N-[4-(N-n-hexyloxycarbonylamidino) phenyl]aminomethyl]benzimidazol-5-yl-carboxylicacid-N-(2-pyridyl)-N-(2-ethoxy carbonylethyl) amide (herein after referred as dabigatran etexilate) and further conversion to its mesylate salt is not disclosed. The purity & yield of dabigatran etexilate prepared as per the disclosed process is not satisfactory, and also the said process involves chromatographic purification. As the chromatographic purification is expensive and difficult to implement on the large scale. Hence the said process is not suitable for commercial scale up.

Moreover, the said process involves the usage of dabigatran hydrochloride, which degrades to form impurities and results in the formation of dabigatran etexilate with low purity. In view of intrinsic fragility of dabigatran hydrochloride, there is a need in the art to develop a stable salt form of 1-methyl-2-[N-[4-amidinophenyl]aminomethyl]benzimidazol-5-yl-carboxylicacid-N-(2-pyridyl)-N-(2-ethoxycarbonyl ethyl)amide, which enhances the purity of the final compound.

The process for the preparation of mesylate salt of dabigatran etexilate and its polymorphic forms was disclosed in US 2005/234104. The disclosed process involves the reaction of dabigatran etexilate with methane sulphonic acid in acetone to provide dabigatran etexilate mesylate. The purity of the obtained crystalline dabigatran etexilate mesylate was not satisfactory i.e., around 97-98% by HPLC. There is no specific purification process disclosed for the purification of dabigatran etexilate mesylate.

Hence there is a need in the art to develop an improved process for the preparation of dabigatran etexilate mesylate with a high purity and yield. And also there is a necessity to provide a purification method for dabigatran etexilate mesylate as well as the isolation, characterization and synthesis of impurities formed in the preparation of dabigatran etexilate and its salts.

Dabigatran etexilate mesylate as prepared by the prior art processes may contain 2-(N-(3-ethoxy-3-oxopropyl)-2-((4-(N'-(hexyloxycarbonyl)carbamimidoyl)phenyl amino)methyl)-1-methyl-1H-benzo[d]imidazole-5-carboxamido)pyridine-1-oxide (herein designated as "N-oxide impurity"); 3-(2-((4-(N'-(hexyloxycarbonyl)carbamimidoyl)phenylamino)methyl)-1-methyl-N-(pyridin-2-yl)-1H-benzo[d] imidazole-5-carboxamido) propanoic acid (herein designated as "Acid impurity") as impurities and represented by the following structural formula:

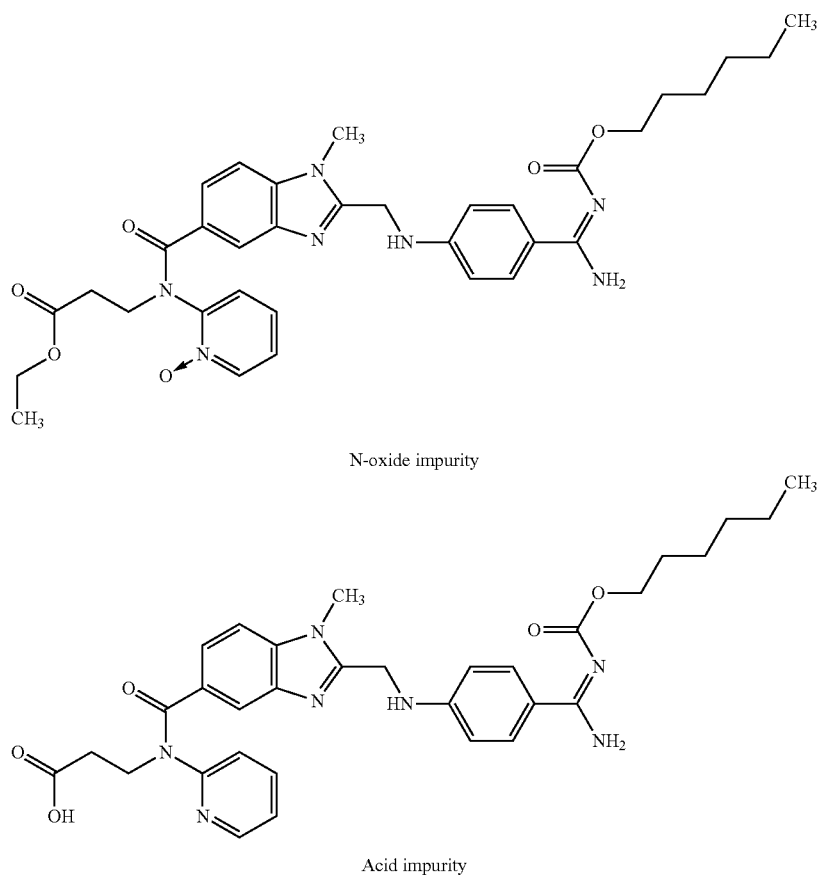

N-oxide impurity

Acid impurity

Other than the above impurities, two more impurities are observed in HPLC at 0.845 RRT and 1.278 RRT respectively. The impurity at 0.845 RRT is herein designated as impurity-X and impurity at 1.278 RRT is herein designated as Impurity-Y. In the present invention N-oxide and acid impurities were isolated and characterized.

ADVANTAGES OF THE PRESENT INVENTION

Provides the usage of novel carbamate inducing agent in the synthesis of Dabigatran etexilate.
Provides in-situ preparation of carbamate inducing agent.
Utilizing a novel technology for the carbamate formation in the synthesis of Dabigatran etexilate.
Provides oxalate salt of 1-methyl-2-[N-[4-amidinophenyl] amino methyl]benzimidazol-5-yl-carboxylicacid-N-(2-pyridyl)-N-(2-ethoxycarbonylethyl) amide to reduce the impurities formed during the preparation of dabigatran etexilate.
Provides pure Dabigatran etexilate without using any additional purification steps.
Provides Dabigatran etexilate mesylate, which is substantially free of acid and N-Oxide impurities
Provides simple, safer and economic process for the preparation of Dabigatran etexilate.

BRIEF DESCRIPTION OF THE INVENTION

The present invention is to provide an improved process for the preparation of dabigatran etexilate mesylate compound of formula-1a in pure form, which ameliorates the problems of the prior art. The process of the present invention is simple, operates in moderate reaction conditions, yields highly pure dabigatran etexilate mesylate compound of formula-1a.

The first aspect of the present invention is to provide novel acid addition salts of 1-methyl-2-[N-[4-amidinophenyl]aminomethyl]benzimidazol-5-yl-carboxylicacid-N-(2-pyridyl)-N-(2-ethoxycarbonylethyl)amide compound of general formula-6, as intermediates for preparing dabigatran etexilate compound of formula-1 or its pharmaceutically acceptable salt, preferably mesylate salt compound of formula-1a.

The second aspect of the present invention is to provide a process for the preparation of novel acid addition salts of 1-methyl-2-[N-[4-amidinophenyl]aminomethyl]benzimidazol-5-yl-carboxylicacid-N-(2-pyridyl)-N-(2-ethoxycarbonyl ethyl)amide compound of general formula-6.

The third aspect of the present invention is to provide a novel crystalline form of 1-methyl-2-[N-[4-amidinophenyl] aminomethyl]benzimidazol-5-yl-carboxylicacid-N-(2-pyridyl)-N-(2-ethoxycarbonylethyl)amide oxalate compound of formula-6a, herein designated as crystalline form-M.

The fourth aspect of the present invention is to provide a process for the purification of 1-methyl-2[N-[4-amidinophenyl]aminomethyl]benzimidazol-5-yl-carboxylicacid-N-(2-pyridyl)-N-(2-ethoxycarbonylethyl)amide compound of formula-5.

The fifth aspect of the present invention is to provide a novel process for the preparation of crystalline form-I of dabigatran etexilate mesylate compound of formula-1a.

The sixth aspect of the present invention is to provide an improved process for the preparation of dabigatran etexilate mesylate compound of formula-1a.

The seventh aspect of the present invention is to provide an improved process for the preparation of dabigatran etexilate compound of formula-1, which comprising of:
a) Reacting n-hexanol compound of formula-2 with N,N-carbonyldiimidazole compound of formula-3 in a suitable solvent to provide hexyl 1H-imidazole-1-carboxylate compound of formula-4,
b) reacting the compound of formula-4 with 1-methyl-2-[N-[4-amidinophenyl]aminomethyl]benzimidazol-5-yl-carboxylicacid-N-(2-pyridyl)-N-(2-ethoxycarbonylethyl) amide compound of formula-5 or its acid addition salts compound of general formula-6 in presence of a base in a suitable solvent to provide dabigatran etexilate compound of formula-1.

The eighth aspect of the present invention is to provide an improved process for the preparation of dabigatran etexilate compound of formula-1, which comprising of:
a) Reacting n-hexanol compound of formula-2 with N,N-carbonyldiimidazole, compound of formula-3 in a suitable solvent to provide hexyl 1H-imidazole-1-carboxylate compound of formula-4,
b) reacting the compound of formula-4 in-situ with 1-methyl-2-[N-[4-amidinophenyl]aminomethyl]benzimidazol-5-yl-carboxylicacid-N-(2-pyridyl)-N-(2-ethoxycarbonylethyl) amide compound of formula-5 or its acid addition salts compound of general formula-6 in presence of a base in a suitable solvent to provide dabigatran etexilate compound of formula-1.

The ninth aspect of the present invention is to provide 2-(N-(3-ethoxy-3-oxopropyl)-2-((4-(N-(hexyloxycarbonyl) carbamimidoyl)phenylamino)methyl)-1-methyl-1H-benzo[d]imidazole-5-carboxamido)pyridine-1-oxide (N-oxide impurity) and 3-(2-((4-(N'-(hexyloxycarbonyl)carbamimidoyl)phenylamino)methyl)-1-methyl-N-(pyridin-2-yl)-1H-benzo[d]imidazole-5-carboxamido) propanoic acid (Acid impurity). The present inventors isolated and characterized the said impurities which were observed in the preparation of dabigatran etexilate mesylate.

The tenth aspect of the present invention is to provide a purification process for dabigatran etexilate mesylate compound of formula-1a, which comprises of the following steps:
a) Dissolving the dabigatran etexilate mesylate compound of formula-1a in a suitable solvent by heating,
b) subjecting the reaction mixture to carbon treatment,
c) filtering the reaction mixture,
d) cooling the reaction mixture and stirring,
e) filtering off the obtained solid and washing with a suitable solvent,
f) drying the solid to obtain pure compound of formula-1a.

The eleventh aspect of the present invention is to provide a purification process for dabigatran etexilate mesylate compound of formula-1a, which comprises of the following steps:
a) Dissolving the dabigatran etexilate mesylate compound of formula-1a in a suitable solvent at suitable temperature,
b) optionally subjecting the solution to carbon treatment,
c) adding suitable anti-solvent to precipitate the product,
d) filtering off the obtained solid and washing with a suitable solvent,
e) drying the solid to obtain pure compound of formula-1a.

The twelfth aspect of the present invention is to provide an improved process for the preparation of highly pure dabigatran etexilate mesylate compound of formula-1a, which comprises of the following steps:
a) Reacting 1-methyl-2-[N-[4-amidinophenyl]aminomethyl] benzimidazol-5-yl-carboxylicacid-N-(2-pyridyl)-N-(2-ethoxycarbonylethyl)amide para toluene sulfonate compound of formula-6b with hexyl chloroformate in presence of a base in a suitable solvent to provide 1-methyl-2-[N-[4-(N-n-hexyloxycarbonyl amidino)phenyl]aminomethyl] benzimidazol-5-yl-carboxylicacid-N-(2-pyridyl)-N-(2-ethoxy carbonylethyl)amide compound of formula-1,
b) treating the compound of formula-1 with methane sulfonic acid in a suitable solvent to provide the compound of formula-1a,
c) dissolving the obtained compound of formula-1a in a suitable solvent by heating,
d) subjecting the reaction mixture to carbon treatment,
e) filtering the reaction mixture,
f) cooling the reaction mixture and stirring,
g) filtering off the obtained solid and washing with a suitable solvent,
h) drying the solid to obtain highly pure compound of formula-1a.

BRIEF DESCRIPTION OF DRAWINGS

FIG. 1: Illustrates the powder X-ray diffraction of crystalline form-M of 1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-6a.

FIG. 2: Illustrates the DSC thermogram of crystalline form-M of 1-methyl-2-[N-[4-amidinophenyl]aminomethyl] benzimidazol-5-yl-carboxylicacid-N-(2-pyridyl)-N-(2-ethoxycarbonylethyl)amide oxalate compound of formula-6a.

FIG. 5: Illustrates the powder X-ray diffraction of crystalline form-I of Dabigatran etexilate mesylate compound of formula-1a.

DETAILED DESCRIPTION OF THE INVENTION

Figure 1:
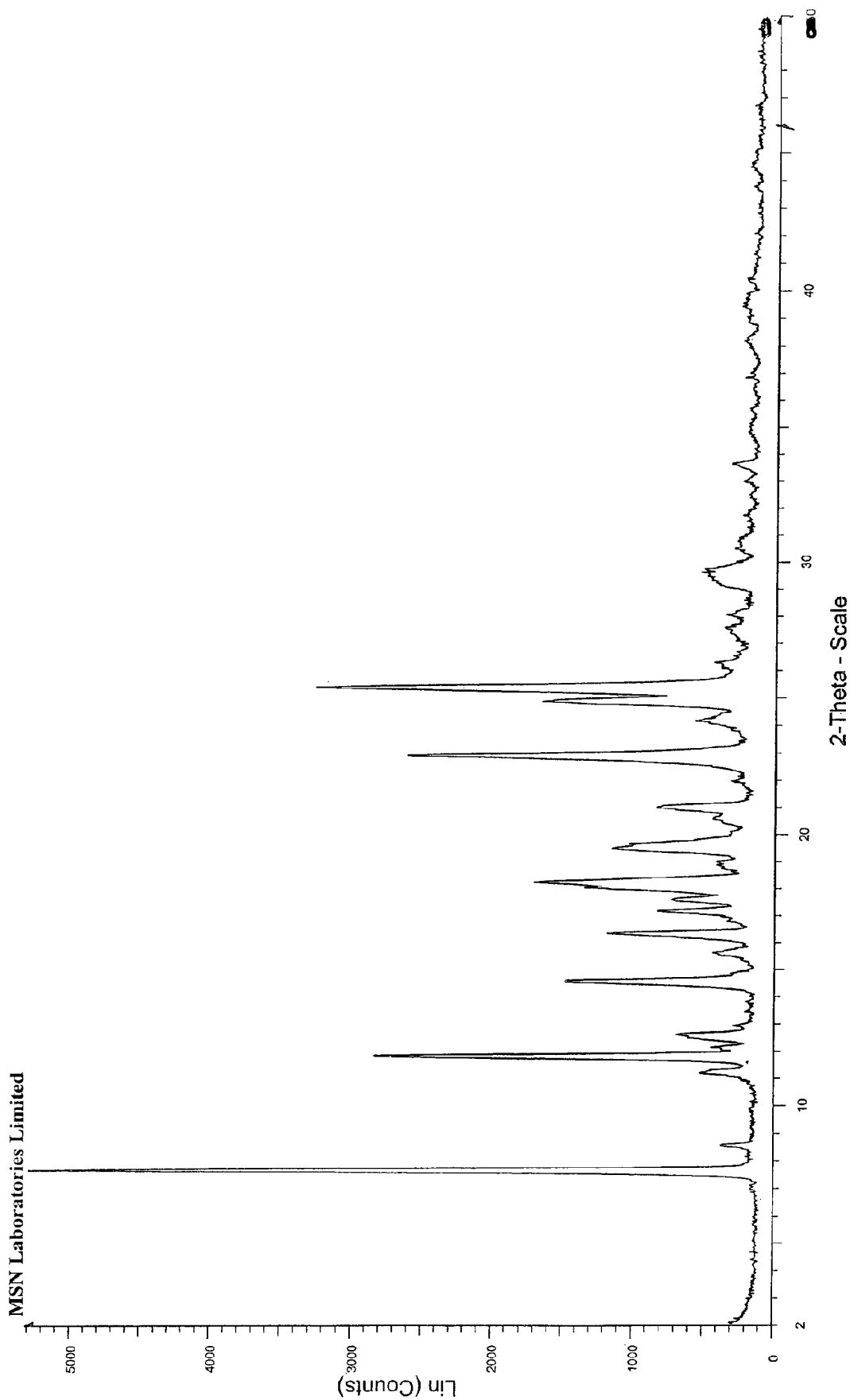

As used herein the present invention the term "suitable solvents" refers to solvents selected from "ester solvents" like ethyl acetate, methyl acetate, isopropyl acetate; "ether solvents" like tetrahydrofuran, diethyl ether, methyl tert-butyl ether, 1,4-dioxane, 1,2-dimethoxy ethane and the like; "hydrocarbon solvents" like toluene, hexane, heptane, perfluorobenzene and cyclohexane; "polar aprotic solvents" like dimethyl acetamide, dimethyl formamide, dimethyl sulfoxide; "ketone solvents" like acetone, methyl ethyl ketone, methyl isobutyl ketone, 4-hydroxy-4-methyl pentanone; "alcoholic solvents" like methanol, ethanol, n-propanol, isopropanol, n-butanol and isobutanol; "chloro solvents" like dichloro methane, chloroform and dichloro ethane; "nitrile solvents" like acetonitrile and propionitrile; "nitro solvents" like nitro methane, nitro ethane and the like; polar solvents like water; and mixtures thereof.

As used herein the present invention the term "suitable bases" refers to the bases selected from inorganic bases like alkali metal hydroxides such as lithium hydroxide, sodium hydroxide, potassium hydroxide; alkali metal alkoxides such as sodium methoxide, sodium ethoxide, sodium tert-butoxide, potassium tert-butoxide; alkali metal carbonates like sodium carbonate, potassium carbonate; and alkali metal bicarbonates like sodium bicarbonate and potassium bicarbonate; and organic bases like triethylamine, isopropyl ethylamine, diisopropyl amine, diisopropyl ethylamine, N-methyl morpholine, piperidine, pyridine and their mixtures thereof.

The term "acid" herein the present invention is selected from inorganic acids such as hydrochloric acid, hydrobromic acid, sulfuric acid, phosphoric acid and the like; organic acids such as methane sulfonic acid, 2,5-dihydroxy benzoic acid, ethanedisulfonic acid, p-toluene sulfonic acid (PTSA), benzene sulfonic acid, ethane disulfonic acid, ethane sulfonic acid, naphthalene disulfonic acid, naphthalene-2-sulfonic acid, camphor sulfonic acid, acetic acid, oxalic acid, fumaric acid, maleic acid, oleic acid, malic acid, adipic acid, stearic acid, cinnamic acid, succinic acid, malonic acid, mandelic acid, palmitic acid, lactic acid, citric acid, tartaric acid, gentisic acid, cyclamic acid, D-glucuronic acid, glycolic acid, isethionic acid, saccharine, salicylic acid, naphthalene-1,5-disulfonic acid and the like.

1-methyl-2-[N-[4-amidinophenyl]aminomethyl]benzimidazol-5-yl-carboxylic acid-N-(2-pyridyl)-N-(2-ethoxycarbonylethyl)amide compound of formula-5 used in the present invention is prepared from the any known methods in the prior art.

The main objective of the present invention is to provide highly pure dabigatran etexilate mesylate compound of formula-1a. Further, the present invention also provides novel acid addition salts of 1-methyl-2-[N-[4-amidinophenyl]aminomethyl]benzimidazol-5-yl-carboxylicacid-N-(2-pyridyl)-N-(2-ethoxycarbonylethyl)amide compound of general formula-6, preferably oxalate salt compound of formula-6a, useful for the synthesis of highly pure dabigatran etexilate mesylate compound of formula-1a.

In another object of the present invention provides a novel technology for the formation of carbamate in the preparation of dabigatran etexilate compound of formula-1 and the present invention also provides novel process for the purification of dabigatran etexilate mesylate compound of formula-1a.

The first aspect of the present invention is to provide novel acid addition salts of 1-methyl-2-[N-[4-amidinophenyl]aminomethyl]benzimidazol-5-yl-carboxylicacid-N-(2-pyridyl)-N-(2-ethoxycarbonylethyl)amide compound of general formula-6, an intermediate compound used in the preparation of dabigatran etexilate mesylate compound of formula-1a.

Wherein the acid is selected from oxalic acid, 2,5-dihydroxy benzoic acid, benzene sulfonic acid, cyclamic acid, ethane sulfonic acid, ethanedisulfonic acid, D-glucaronoic acid, glycolic acid, mandelic acid, palmitic acid, oleic acid, stearic acid, cinnamic acid, camphor sulfonic acid, adipic acid, naphthalene-2-sulfonic acid and naphthalene-1,5-disulfonic acid.

Further, a preferred embodiment of the present invention is to provide an oxalate salt of 1-methyl-2-[N-[4-amidinophenyl]aminomethyl]benzimidazol-5-yl-carboxylicacid-N-(2-pyridyl)-N-(2-ethoxycarbonylethyl)amide compound of formula-6a.

The second aspect of the present invention is to provide a process for the preparation of novel acid addition salts of 1-methyl-2-[N-[4-amidinophenyl]amino methyl]benzimidazol-5-yl-carboxylicacid-N-(2-pyridyl)-N-(2-ethoxycarbonylethyl) amide compound of general formula-6, which comprising of:

a) Treating the 1-methyl-2-[N-[4-amidinophenyl]aminomethyl]benzimidazol-5-yl-carboxylicacid-N-(2-pyridyl)-N-(2-ethoxycarbonylethyl)amide compound of formula-5 with a suitable acid in a suitable solvent to provide its corresponding acid addition salt compound of general formula-6, b) isolating the solid obtained in step-a) to provide compound of general formula-6.

Wherein, in step-a) the suitable acid is selected from oxalic acid, 2,5-dihydroxy benzoic acid, benzene sulfonic, acid, cyclamic acid, ethane sulfonic acid, ethanedisulfonic acid, D-glucaronoic acid, glycolic acid, mandelic acid, palmitic acid, oleic acid, stearic acid, cinnamic acid, camphor sulfonic acid, adipic acid, naphthalene-2-sulfonic acid and naphthalene-1,5-disulfonic acid the suitable solvent is selected from alcoholic solvents, chloro solvents, ether solvents, nitro solvents, ketone solvents, ester solvents, nitrile solvents, hydrocarbon solvents.

In a preferred embodiment of the present invention is to provide a process for the preparation of 1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-6a comprising of, a) Treating the 1-methyl-2-[N-[4-amidinophenyl]aminomethyl]benzimidazol-5-yl-carboxylicacid-N-(2-pyridyl)-N-(2-ethoxycarbonylethyl)amide compound of formula-5 with oxalic acid in ethanol to provide 1-methyl-2-[N-[4-amidino phenyl]aminomethyl]benzimidazol-5-yl-carboxylicacid-N-(2-pyridyl)-N-(2-ethoxycarbonylethyl) amide oxalate compound of formula-6a, b) isolating the solid obtained in step-a) to provide pure compound of formula-6a.

The advantage of making an oxalate salt of 1-methyl-2-[N-[4-amidinophenyl]aminomethyl]benzimidazol-5-yl-carboxylicacid-N-(2-pyridyl)-N-(2-ethoxycarbonyl ethyl) amide compound of formula-6a is to reduce the impurities formed during the preparation of dabigatran etexilate, according to the prior art process. Further, isolation of 1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-6a as a crystalline form provides highly pure compound of formula-6a (Purity 99% by HPLC), dabigatran etexilate compound of formula-1 (Purity 99.58 by HPLC) and its mesylate salt compound of formula-1a (Purity 99.64 by HPLC).

We, the present inventors have surprisingly found that, the 1-methyl-2-[N-[4-amidinophenyl]aminomethyl]benzimidazol-5-yl-carboxylicacid-N-(2-pyridyl)-N-(2-ethoxycarbonylethyl)amide oxalate salt compound of formula-6a can be isolated as a pure solid.

It has been found that the oxalate salt of 1-methyl-2-[N-[4-amidinophenyl]aminomethyl]benzimidazol-5-yl-carboxylicacid-N-(2-pyridyl)-N-(2-ethoxycarbonyl ethyl) amide compound of formula-6a has certain advantages over the other salts reported in the prior-art. Moreover, the synthesis of oxalate salt of compound of formula-6a is simple, ecofriendly, robust and well suited on commercial scale up.

The third aspect of the present invention is to provide a novel crystalline form of 1-methyl-2-[N-[4-amidinophenyl]aminomethyl]benzimidazol-5-yl-carboxylicacid-N-(2-pyridyl)-N-(2-ethoxycarbonylethyl)amide oxalate salt compound of formula-6a, herein designated as crystalline form-M. Further, the crystalline form-M of oxalate salt of compound of formula-6a in accordance with the present invention is characterized by its powder XRD pattern having peaks at about 7.6, 11.7, 14.5, 18.0, 18.2, 22.8, 24.8 and 25.3±0.2 degrees two-theta; Further the PXRD pattern of 1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-6a of the present invention is shown in FIG. 1.

Figure 2:
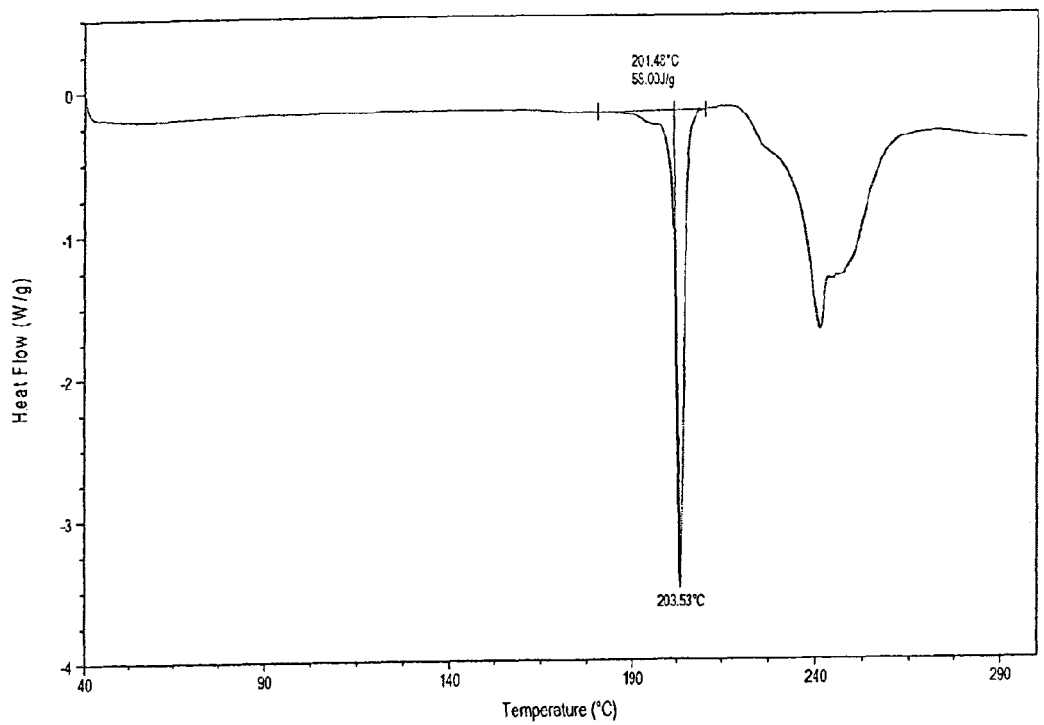

The crystalline form-M of 1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-6a is further characterized by DSC thermogram showing endotherm at about 203.53° C. and is shown in FIG. 2.

The fourth aspect of the present invention is to provide a process for purification of 1-methyl-2-[N-[4-amidinophenyl] aminomethyl]benzimidazol-5-yl-carboxylicacid-N-(2-pyridyl)-N-(2-ethoxycarbonylethyl)amide compound of formula-5, comprising of:
a) Treating the 1-methyl-2-[N-[4-amidinophenyl]aminomethyl]benzimidazol-5-yl-carboxylicacid-N-(2-pyridyl)-N-(2-ethoxycarbonylethyl)amide compound of formula-5 with a suitable acid in a suitable solvent to provide acid addition salt compound of general formula-6,
b) treating the compound of general formula-6 with a suitable base in suitable solvent and isolating the compound to provide pure compound of formula-5.

Wherein, in step-a) the suitable acid and solvent used are same as defined in the step-a) of second aspect;

in step-b) is organic solvent selected from ether solvents like tetrahydrofuran, methyl tert-butyl ether, diethylether, ester solvents like methyl acetate, ethylacetate, isopropylacetate; ketone solvents like acetone, propanone, methylethyl ketone, methylisobutylketone; polar aprotic solvents like dimethylformamide, acetonitrile, or mixtures of water and organic solvent; and the base is selected from alkali metal carbonates like sodium carbonate, potassium carbonate; alkali metal bicarbonates like sodium bicarbonate and potassium bicarbonate and the like.

Further, in a preferred embodiment of the present invention provides a process for purification of 1-methyl-2-[N-[4-amidinophenyl]aminomethyl]benzimidazol-5-yl-carboxylicacid-N-(2-pyridyl)-N-(2-ethoxycarbonylethyl)amide compound of formula-5, comprising of:
a) Treating the 1-methyl-2-[N-[4-amidinophenyl]aminomethyl]benzimidazol-5-yl-Carboxylicacid-N-(2-pyridyl)-N-(2-ethoxycarbonylethyl)amide compound of formula-5 with oxalic acid in ethanol to provide oxalate salt compound of formula-6a,
b) treating the compound of formula-6a with potassium carbonate in aqueous acetonitrile and isolating the compound to provide pure compound of formula-5.

Further the present invention also provides a process for the preparation of 1-methyl-2-[N-[4-amidinophenyl]aminomethyl]benzimidazol-5-yl-carboxylicacid-N-(2-pyridyl) N-(2-ethoxycarbonylethyl)amide compound of formula-5 or its hydro halide salt compounds of general formula-17 comprising of:
a) Reacting 4-aminobenzonitrile compound of formula-16 with sodium 2-chloroacetate in presence of a suitable base in presence or absence of phase transfer catalyst in a suitable solvent to provide 2-(4-cyanophenylamino) acetic acid compound of formula-13,
b) condensing the compound of formula-13 with ethyl 3-(3-amino-4-(methylamino)-N-(pyridin-2-yl)benzamido)propanoate compound of formula-12 in presence of carbonyldiimidazole in a suitable solvent to provide 1-methyl-2-[N-(4-cyanophenyl)aminomethyl]benzimidazol-5-yl-carboxylicacid-N-(2-pyridyl)-N-(2-ethoxy carbonyl ethyl) amide compound of formula-14,
c) reacting the compound of formula-14 with ammonium carbonate in presence of Lewis acid and hydrochloride gas in a suitable solvent to provide 1-methyl-2-[N-[4-amidino phenyl]aminomethyl]benzimidazol-5-ylcarboxylicacid-N-(2-pyridyl)-N-(2-ethoxy carbonyl ethyl) amide hydro chloride salt compound of formula-17a.
d) optionally converting the compound of formula-17a into 1-methyl-2-[N-[4-amidino phenyl]aminomethyl]benzimidazol-5-ylcarboxylicacid-N-(2-pyridyl)-N-(2-ethoxy carbonyl ethyl) amide compound of formula-5 by treating with a suitable base in a suitable solvent.

Wherein in step a) the suitable base is selected from alkali metal hydroxides, alkali metal carbonates and alkali metal bicarbonates preferably sodium bicarbonate and the suitable solvent is selected from alcohol solvents, ketone solvents, polar solvents or their mixtures thereof; preferably water; and the suitable phase transfer catalyst is tertiary butyl ammonium bromide;

in step b) the suitable solvent is selected from ether solvents, hydrocarbon, solvents, ester solvents, ketone solvents or their mixtures thereof; preferably tetrahydrofuran;

in step c) the suitable Lewis acid is selected from aluminium chloride ($AlCl_3$), aluminium bromide ($AlBr_3$), boran trifluoride ($BCl_3$), boran trichloride ($BF_3$), Iron(III) chloride ($FeCl_3$), Tin(IV) chloride ($SnCl_4$), calcium chloride dihydrate ($CaCl_2.2H_2O$), calcium chloride ($CaCl_2$) etc; preferably calcium chloride dihydrate; and the suitable solvent is selected from alcohol solvents, ether solvents, ketone solvents or their mixtures thereof; preferably ethanol;

in step d) the suitable base is selected from inorganic bases like alkali metal hydroxides, alkali metal carbonates and alkali metal bicarbonates or organic bases like triethylamine, isopropyl ethylamine, diisopropyl amine, diisopropyl ethylamine, N-methyl morpholine, piperidine, pyridine and the suitable solvent is selected from alcohol solvents, ether solvents, ketone solvents, ester solvents, hydrocarbon solvents, chloro solvents, polar solvents or their mixtures thereof.

The fifth aspect of the present invention is to provide a novel process for the preparation of crystalline form-I of dabigatran etexilate mesylate compound of formula-1a, which comprising of:
a) Dissolving dabigatran etexilate in an ester solvent by heating to a suitable temperature,
b) filtering the reaction mixture,
c) cooling the obtained filtrate and adding an alcoholic solvent to it,
d) adding a solution of methane sulfonic acid in ester solvent to the reaction mixture,
e) stirring the reaction mixture,
f) filtering the solid and washing with an ester solvent,
g) drying the solid to get crystalline form-I of dabigatran etexilate mesylate compound of formula-1a.

In a preferred embodiment of the present invention is to provide a process for the preparation of crystalline form-I of dabigatran etexilate mesylate compound of formula-1a, which comprising of:
a) Dissolving dabigatran etexilate in an ethyl acetate by heating to 40° C.,
a) filtering the reaction mixture and cooling the filtrate to 25-30° C.,
b) adding ethanol to the filtrate,
c) adding a solution of methane sulfonic acid in ethyl acetate to the reaction mixture,
d) stirring the reaction mixture at 25-35° C.,
e) filtering the solid and washing with ethyl acetate,
f) drying the solid to get crystalline form-I of dabigatran etexilate mesylate compound of formula-1a.

The sixth aspect of the present invention is to provide an improved process for the preparation of dabigatran etexilate mesylate compound of formula-1a, which comprising of the following steps:
a) Treating 1-methyl-2-[N-[4-amidinophenyl]aminomethyl] benzimidazol-5-yl-carboxylicacid-N-(2-pyridyl)-N-(2-ethoxycarbonylethyl)amide compound of formula-5 with a suitable acid in a suitable solvent to provide its corresponding acid addition salt compound of general formula-6, b) reacting the compound of general formula-6 with n-hexylchloroformate in presence of a base in a suitable solvent to provide dabigatran etexilate compound of formula-1, c) optionally purifying the compound obtained in step-b) in a suitable solvent to provide pure compound of formula-1, d) treating the pure compound of formula-1 with methane sulfonic acid in a suitable solvent to provide dabigatran etexilate mesylate compound of formula-1a.

Wherein the suitable acid and solvent used in step-a) are same as defined in the step-a) of the fourth aspect;

In step-b) the suitable base and solvent used are same as defined in the step-b) of the fourth aspect;

In step-c) the suitable solvent is selected from chloro solvents, ketone solvents, ester solvents, alcoholic solvents, polar solvents like water and/or mixtures thereof;

In step-d) the suitable solvent is selected from ester solvents, alcoholic solvents or mixtures thereof.

Further a preferred embodiment of the present aspect is to provide an improved process for the preparation of dabigatran etexilate mesylate compound of formula-1a, comprising of:

a) Treating the 1-methyl-2-[N-[4-amidinophenyl]aminomethyl]benzimidazol-5-yl-carboxylicacid-N-(2-pyridyl)-N-(2-ethoxycarbonylethyl)amide compound of formula-5 with oxalic acid in ethanol to provide oxalate salt compound of formula-6a, b) reacting the compound of formula-6a with n-hexylchloroformate in presence of potassium carbonate in aqueous methyl ethyl ketone to provide dabigatran etexilate compound of formula-1 c) treating the compound of formula-1 with methane sulfonic acid in ethyl acetate to provide dabigatran etexilate mesylate compound of formula-1a.

WO98/37075 disclosed the process for the preparation of dabigatran etexilate, which involves the usage of dabigatran hydrochloride salt. Due to the intrinsic fragility of dabigatran hydrochloride, leading to the formation of high impurities resulting the dabigatran etexilate with low purity. Whereas, the present invention involves the usage of oxalate salt of dabigatran, which is stable and provides the dabigatran etexilate with high purity.

Moreover, the process disclosed in WO98/37075 involves the usage of n-hexylchloroformate, which is more expensive. The commercially available n-hexylchloroformate may degrade on long storage and may lead to the formation of impure n-hexylchloroformate, which inturn affects the purity and yield of the final compound.

We, the present inventors after extensive research, were able to find out an alternative for n-hexylchloroformate i.e. hexyl 1H-imidazole-1-carboxylate, which is prepared by using widely available and highly pure n-hexanol and N,N-carbonyldiimidazole. Moreover these n-hexanol and N,N-carbonyldiimidazole are non-toxic and cheaper reagents. Hence the usage of hexyl 1H-imidazole-1-carboxylate compound of formula-4 is more advantageous over n-hexylchloroformate for the preparation of dabigatran etexilate.

The seventh aspect of the present invention is to provide an improved process for the preparation of dabigatran etexilate compound of formula-1, which comprising of:

a) Reacting n-hexanol compound of formula-2

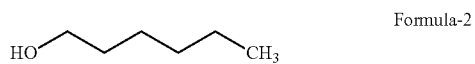

Formula-2 with N,N-carbonyldiimidazole compound of formula-3

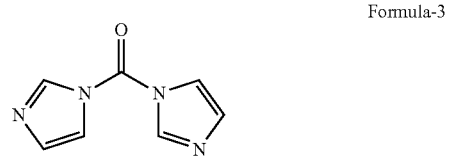 [SMILES: O=C(n1ccnc1)n1ccnc1]

Formula-3 in a suitable solvent to provide n-hexyl 1H-imidazole-1-carboxylate compound of formula-4,

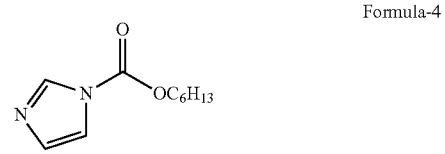

Formula-4 b) reacting the compound of formula-4 with 1-methyl-2-[N-[4-amidinophenyl]aminomethyl]benzimidazol-5-yl-carboxylicacid-N-(2-pyridyl)-N-(2-ethoxy carbonylethyl) amide compound of formula-5

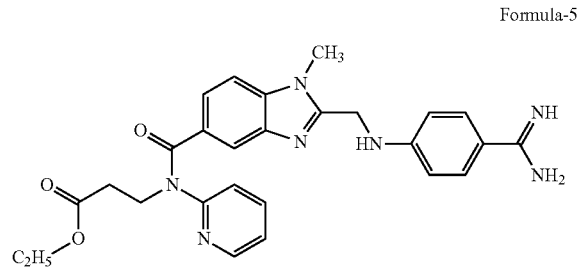 [SMILES: CCOC(=O)CCN(C(=O)c1ccc2c(c1)nc(CNc1ccc(C(=N)N)cc1)n2C)c1ccccn1]

Formula-5 or its salts compound of general formula-6

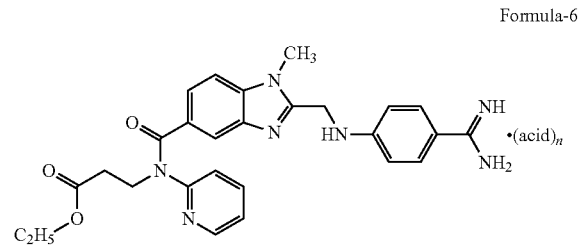

Formula-6

6a) acid = oxalic acid wherein, n is 1 or 2, in presence of a base in a suitable solvent to provide dabigatran etexilate compound of formula-1.

Wherein, in step-a) the suitable solvent is selected from "chloro solvents" like dichloromethane, chloroform, dichloroethane; "ester solvents" like ethyl acetate, methyl acetate, isopropyl acetate; "ether solvents" like tetrahydrofuran, diethyl ether, methyl tert-butyl ether; "ketone solvents" like acetone, methylethylketone, propanone, methylisobutylketone; "polar aprotic solvents" like dimethylformamide, dimethyl acetamide; and "nitrile solvents" like acetonitrile, propionitrile; and in step-b) the suitable solvent is selected from "ether solvents" like tetrahydrofuran, diethyl ether, methyl tert-butyl ether; "ester solvents" like ethyl acetate, methyl acetate, isopropyl acetate; "ketone solvents" like acetone, methylethylketone, propanone, methylisobutylketone; "polar aprotic solvents" like dimethylformamide, dimethyl acetamide; and "nitrile solvents" like acetonitrile, propionitrile, or mixtures of water and organic solvent; and the base is selected from alkali metal carbonates like sodium carbonate, potassium carbonate; alkali metal bicarbonates like sodium bicarbonate and potassium bicarbonate and the like.

The preferred embodiment of the present invention is to provide dabigatran etexilate compound of formula-1, which comprising of:
a) Reacting n-hexanol compound of formula-2 with N,N-carbonyldiimidazole compound of formula-3 in dichloromethane to provide n-hexyl 1H-imidazole-1-carboxylate compound of formula-4,
b) reacting the compound of formula-4 with 1-methyl-2-[N-[4-amidinophenyl]aminomethyl]benzimidazol-5-yl-carboxylicacid-N-(2-pyridyl)-N-(2-ethoxy carbonylethyl) amide compound of formula-5 in presence of potassium carbonate in aqueous acetonitrile to provide Dabigatran etexilate compound of formula-1.

The other preferred embodiment of the present invention is to provide dabigatran etexilate compound of formula-1, which comprising of:
a) Reacting n-hexanol compound of formula-2 with N,N-carbonyldiimidazole compound of formula-3 in dichloromethane to provide n-hexyl 1H-imidazole-1-carboxylate compound of formula-4,
b) reacting the compound of formula-4 with 1-methyl-2-[N-[4-amidinophenyl]aminomethyl]benzimidazol-5-yl-carboxylicacid-N-(2-pyridyl)-N-(2-ethoxy carbonylethyl) amide oxalate compound of formula-6a Formula-6a

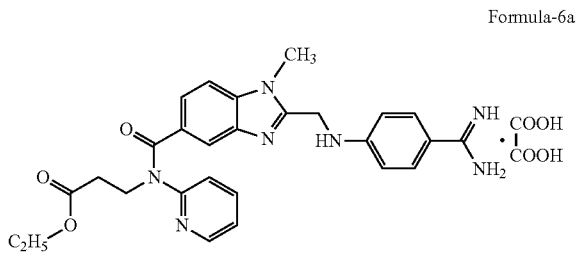

in presence of potassium carbonate in aqueous acetonitrile to provide Dabigatran etexilate compound of formula-1.

The eighth aspect of the present invention is to provide an improved process for the preparation of dabigatran etexilate compound of formula-1, which comprising of:
a) Reacting n-hexanol compound of formula-2 with N,N-carbonyldiimidazole compound of formula-3 in a suitable solvent to provide n-hexyl 1H-imidazole-1-carboxylate compound of formula-4, b) reacting the compound of formula-4 in-situ with 1-methyl-2-[N-[4-amidinophenyl]aminomethyl]benzimidazol-5-yl-carboxylicacid-N-(2-pyridyl)-N-(2-ethoxycarbonylethyl) amide compound of formula-5 or its salts compound of general formula-6 in presence of a base in a suitable solvent to provide Dabigatran etexilate compound of formula-1.

Wherein, the suitable solvent used in step-a) and the suitable solvent and base used in step-b) are same as defined in the step-a) and step-b) of the seventh aspect respectively.

In the above aspects of seventh & eighth, the step b) is carried out at a temperature between 0-100° C., preferably at a temperature between 5-55° C., more preferably at a temperature between 10-45° C., most preferably at a temperature between 25-35° C. for a period of 9-24 hours.

The solvent used in step-a) of the above seventh & eighth aspects is in an amount ranging from 2-10 volumes, preferably from 3-7 volumes, most preferably 5 volumes to compound of formula-5 or compound of general formula-6.

The solvent used in step-b) of the above seventh & eighth aspects is in an amount ranging from 5-50 volumes, preferably from 10-40 volumes, most preferably 20 volumes to compound of formula-5 or compound of general formula-6 and the ratio of organic solvent and water is between 2:8 to 8:2, preferably is 6:4.

The n-hexanol used in the step-a) of $7^{th}$ & $8^{th}$ aspects of the present invention is in the mole proportions between 0.8-6, preferably between 1-3, most preferably 1.5 per one mole of compound of formula-5 or compound of general formula-6.

The N,N-carbonyldiimidazole used in the step-a) of $7^{th}$ & $8^{th}$ aspects of the present the present invention is in the mole proportions between 0.8-6, preferably between 1-3, most preferably 1.75 per one mole of compound of formula-5 or compound of general formula-6.

The base employed in step-b) of $7^{th}$ & $8^{th}$ aspects of the present invention is in the mole proportions between 0.8-10, preferably between 1-8, most preferably 5 per one mole of compound of formula-5 or compound of general formula-6.

The present invention provides a simple, safer, robust, economic process for the preparation of hexyl 1H-imidazole-1-carboxylate compound of formula-4, which is well suited for commercial scale up. This compound may be further isolated as a solid using a suitable solvent.

We, the first inventor found that the usage of hexyl 1H-imidazole-1-carboxylate compound of formula-4 for carbamate preparation in the synthesis of dabigatran etexilate, which is well suited for commercial scale up.

US 2010210845 disclosed dabigatran etexilate with purity greater than 99%, which requires additional purification steps in obtaining such purity. It is surprisingly found that, when we utilize the hexyl 1H-imidazole-1-carboxylate compound of formula-4 for carbamate formation, it results in the formation of dabigatran etexilate with enhanced purity i.e. greater than 99%, preferably 99.5%, without any additional purification steps.

The ninth aspect of the present invention is to provide 2-(N-(3-ethoxy-3-oxopropyl)-2-((4-(N'-(hexyloxycarbonyl) carbamimidoyl)phenylamino)methyl)-1-methyl-1H-benzo[d]imidazole-5-carboxamido)pyridine-1-oxide (N-oxide impurity) and 3-(2-((4-(N'-(hexyloxycarbonyl)carbamimidoyl)phenylamino)methyl)-1-methyl-N-(pyridin-2-yl)-1H-benzo[d]imidazole-5-carboxamido)propanoic acid (Acid impurity), compounds, which were observed as impurities in the synthesis of 1-methyl-2-[N-[4-amidinophenyl]aminomethyl]benzimidazol-5-yl-carboxylicacid-N-(2-pyridyl)-N-(2-ethoxycarbonyl ethyl)amide and its pharmaceutically acceptable salts.

The N-Oxide and acid impurities of the present invention are characterized by NMR, IR and Mass spectral data.

The N-oxide impurity was prepared by reacting dabigatran etexilate with a suitable oxidizing agent like hydrogen peroxide in a suitable solvent. The said impurity was observed at 1.118 RRT in HPLC.

The acid impurity was prepared by hydrolyzing the dabigatran etexilate with a suitable milder base in a suitable solvent. The said impurity was observed at 0.477 RRT in HPLC.

In addition to the above impurities, the dabigatran etexilate and its salts prepared by the prior art processes contain two more impurities which are observed in HPLC at 0.845 RRT (Impurity-X) and 1.278 RRT (Impurity-Y) respectively. The impurity at 0.845 RRT is having mass m/z value of 655 as characterized by LC-MS (Liquid chromatography-mass spectrum) analysis.

The tenth aspect of the present invention is to provide a purification process for dabigatran etexilate mesylate compound of formula-1a, which comprises of the following steps:
a) Dissolving the dabigatran etexilate mesylate compound of formula-1a in a suitable solvent selected from ketone solvents, alcohol solvents, ester solvents or mixtures thereof by heating,
b) subjecting the reaction mixture to carbon treatment,
c) filtering the reaction mixture,
d) cooling the filtrate and stirring,
e) filtering off the solid obtained in step-d) and washing with a suitable solvent,
f) drying the solid to obtain pure dabigatran etexilate mesylate compound of formula-1a.

In a preferred embodiment of the present invention, the process for the purification of dabigatran etexilate mesylate compound of formula-1a, comprises of:
a) Dissolving the dabigatran etexilate mesylate compound of formula-1a in a mixture of methanol and acetone at 50-55° C.,
b) subjecting the reaction mixture to carbon treatment,
c) filtering the reaction mixture,
d) cooling the filtrate to 20-25° C. and stirring,
e) further cooling the filtrate to 0-5° C. and stirring, filtering off the solid obtained in step-e) and washing with acetone,
g) drying the solid to obtain pure dabigatran etexilate mesylate compound of formula-1a.

The eleventh aspect of the present invention is to provide a purification process for dabigatran etexilate mesylate compound of formula-1a, which comprises of the following steps,
a) Dissolving the dabigatran etexilate mesylate compound of formula-1a in a suitable alcohol solvent at a suitable temperature,
b) optionally subjecting the reaction mixture to carbon treatment,
c) adding suitable anti-solvent selected from ester solvent or ketone solvent to precipitate the product,
d) filtering off the obtained solid and washing with suitable ketone solvent or ester solvent,
e) drying the solid to obtain pure compound of formula-1a.

In a preferred embodiment of the present invention, the process for the purification of dabigatran etexilate mesylate compound of formula-1a comprises of,
a) Dissolving the dabigatran etexilate mesylate compound of formula-1a in methanol at 25-30° C.,
b) subjecting the reaction mixture to carbon treatment,
c) adding acetone to the obtained filtrate,
d) filtering the reaction mixture,
e) cooling the reaction mixture to 0-5° C. and stirring,
f) filtering off the obtained solid and washing with acetone,
g) drying the solid to obtain pure dabigatran etexilate mesylate compound of formula-1a.

Figure 3:
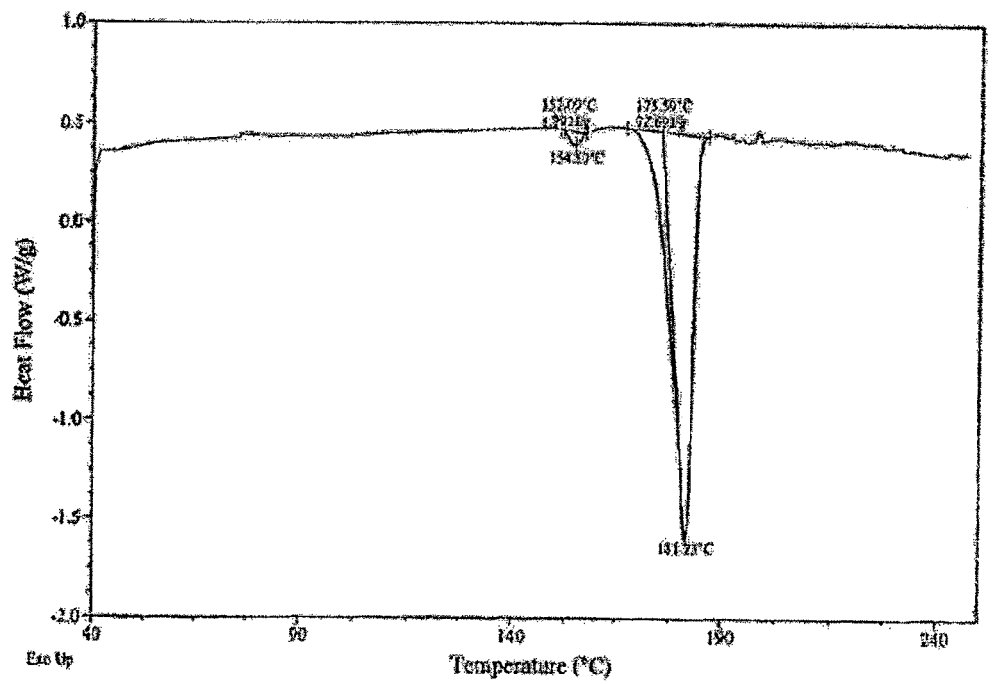
FIG. 3: DSC chromatogram of dabigatran etexilate mesylate obtained as per the example-13.
Figure 4:
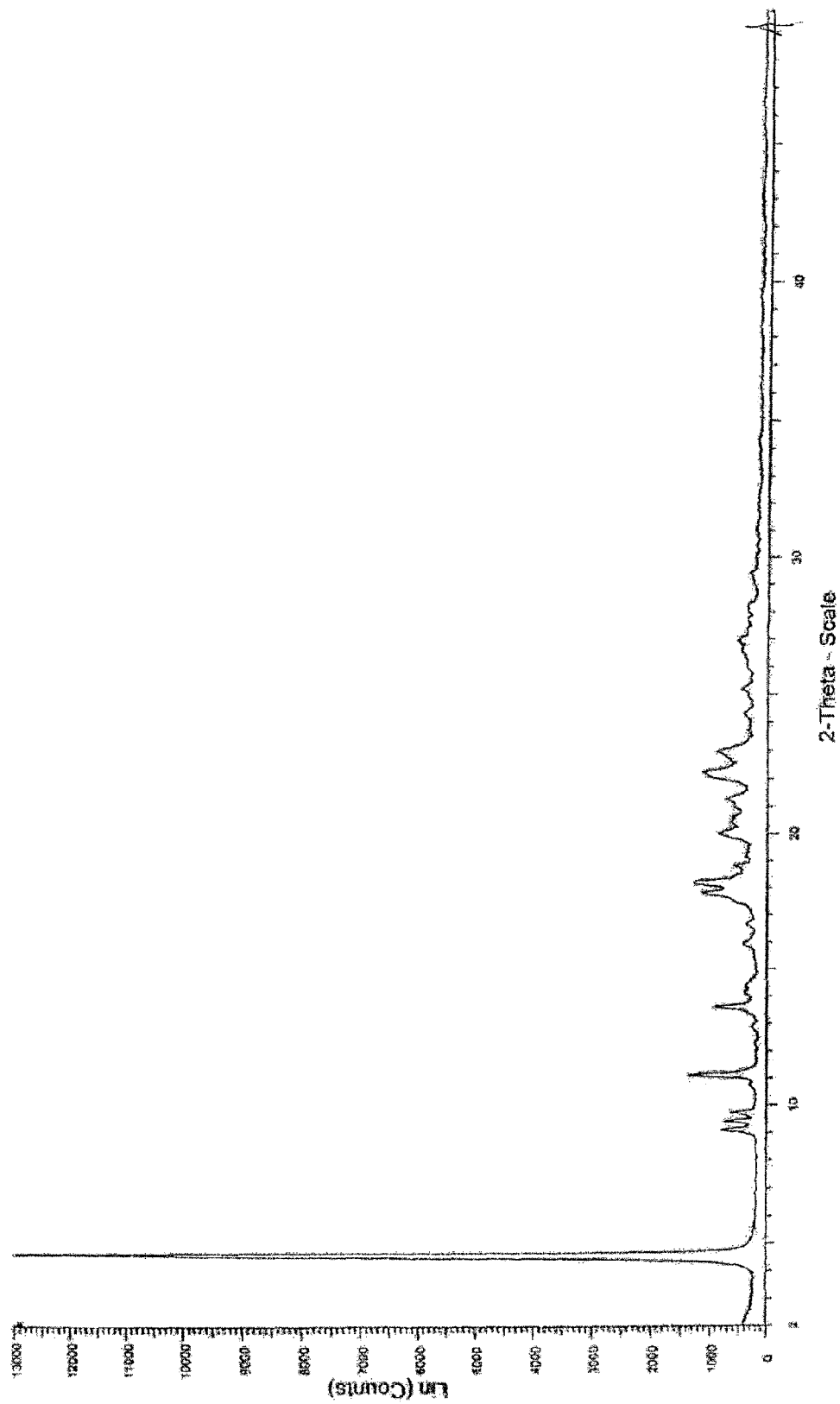
FIG. 4: Powder X-ray diffraction pattern of dabigatran etexilate mesylate obtained as example-13.

According to the tenth and eleventh aspects of the present invention, the PXRD and DSC thermogram of dabigatran etexilate mesylate are shown in the FIGS. 3&4 respectively.

The twelfth aspect of the present invention is to provide a process for the preparation of dabigatran etexilate mesylate compound of formula-1a, which comprises of the following steps:
a) Reacting 1-methyl-2-[N-[4-amidinophenyl]aminomethyl]benzimidazol-5-yl-carboxylicacid-N-(2-pyridyl)-N-(2-ethoxycarbonylethyl)amide paratoluene sulfonate compound of formula-6b,

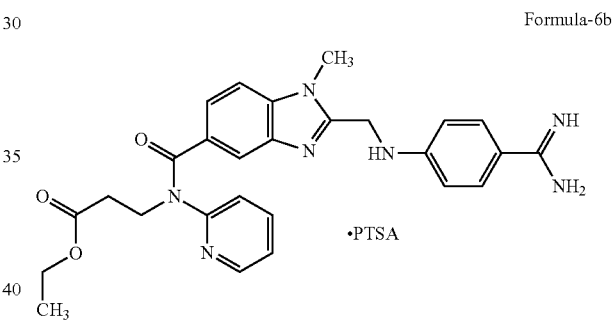

Formula-6b with hexyl chloroformate in presence of a suitable base in a suitable solvent provides 1-methyl-2-[N-[4-(N-n-hexyloxycarbonylamidino)phenyl]amino methyl]benzimidazol-5-yl-carboxylicacid-N-(2-pyridyl)-N-(2-ethoxycarbonyl ethyl)amide compound of formula-1, Formula-1 b) treating the compound of formula-1 with methane sulfonic acid in a suitable solvent to provide the dabigatran etexilate mesylate compound of formula-1a,
c) dissolving the obtained compound of formula-1a in a suitable solvent by heating,
d) subjecting the reaction mixture to carbon treatment,
e) filtering the reaction mixture,
f) cooling the filtrate and stirring,
g) filtering off the obtained solid and washing with a suitable solvent,
h) drying the solid to obtain highly pure dabigatran etexilate mesylate compound of formula-1a.

The dabigatran etexilate mesylate compound of formula-1a prepared as per the prior art process having purity around 97-98% and containing impurities such as N-oxide in the range of 1-1.5%, acid impurity in the range of 1-1.5%, Impurity-X and Y in the range of 0.2-0.8% respectively by HPLC. The said impurities are washed out, even to not detectable level by HPLC by purifying the dabigatran etexilate mesylate compound of formula-1 by the purification process of the present invention.

Dabigatran etexilate mesylate prepared as per the present invention is having purity greater than 99.50% by HPLC; preferably 99.75%; more preferably 99.95% by HPLC.

Dabigatran etexilate mesylate prepared as per the present invention containing less than 0.05% of impurity-X and Impurity-Y; preferably less than 0.01% by HPLC.

Dabigatran etexilate mesylate prepared as per the present invention containing less than 0.1% of "acid impurity" and "N-oxide impurity" by HPLC; preferably less than 0.05% by HPLC; more preferably less than 0.01% by HPLC.

Dabigatran etexilate mesylate prepared as per the present invention is substantially free of acid and N-Oxide impurities.

Dabigatran etexilate mesylate of the present invention can be further micronized or milled to get the desired particle size. Milling or micronization may be performed before drying, or after the completion of drying of the product. Techniques that may be used for particle size reduction include, without limitation, ball, roller and hammer mills, and jet mills.

The related substances of dabigatran etexilate mesylate measured using HPLC with the following chromatographic conditions: Column: Inertsil C-8 (150×4.6 mm, 5μ) or equivalent column. Other parameters of the method are as shown in the following table.

| | |
|---|---|
| Flow | 1.0 mL/minute |
| Elution | Gradient |
| Wavelength | 240 nm |
| Injection volume | 15 mL |
| Oven temperature | Ambient |
| Mobile phase preparation | Mobile phase A: 0.01M ammonium formate in water having pH adjusted to 4.5 with HCOOH + Acetonitrile in the volume ratio of 80:20 |
| | Mobile phase B: Acetonitrile + Water in the volume ratio of 80:20 |
| Diluent | Acetonitrile + Water in the volume ratio of 50:50 |
| Sample concentration | 2.0 mg/1.0 mL |

Further, the said Dabigatran etexilate mesylate can be used in the formation of medicament as an active ingredient for the treatment of thrombosis.

The possible impurities may be formed in the synthesis of Dabigatran etexilate are as follows:

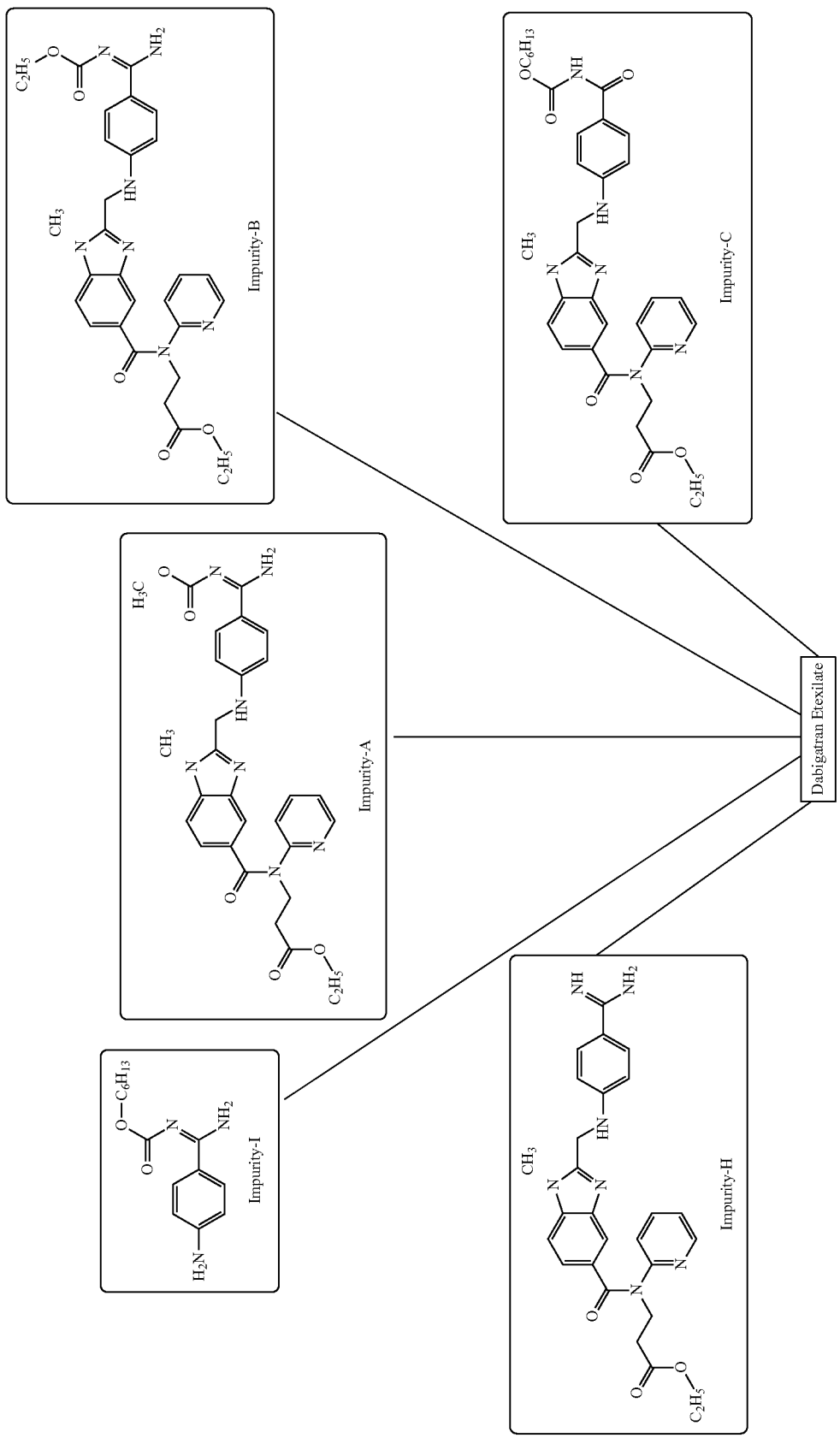

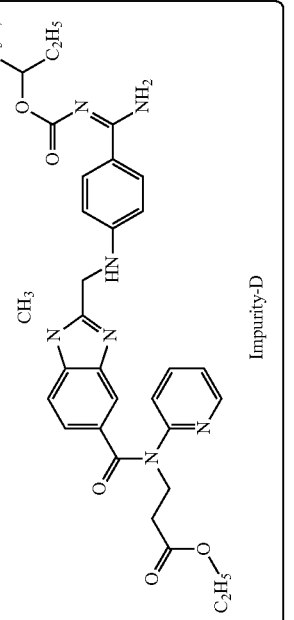
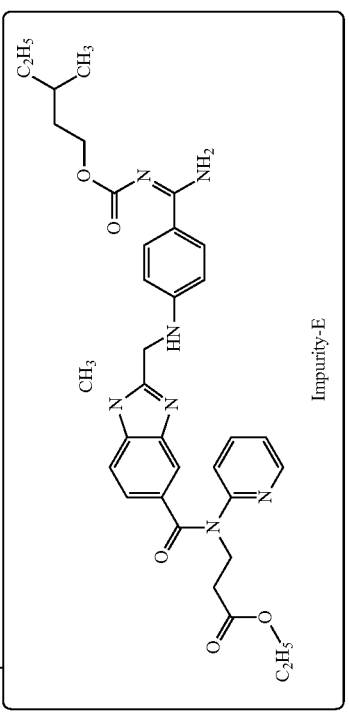
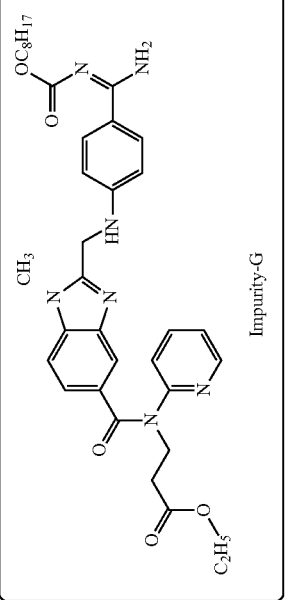
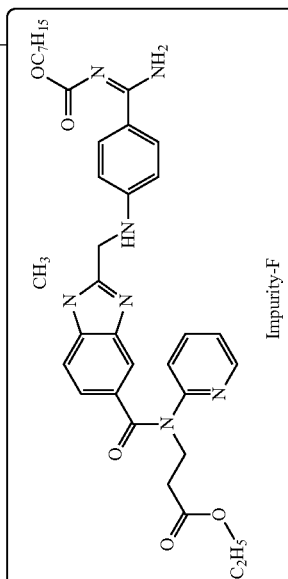

All these impurities are formed due to the presence of impure n-hexanol that is present in commercially available n-hexyl-chloroformate. The present invention controls all these impurities by using pure n-hexanol.
The present invention is schematically represented as follows:
Scheme-1:
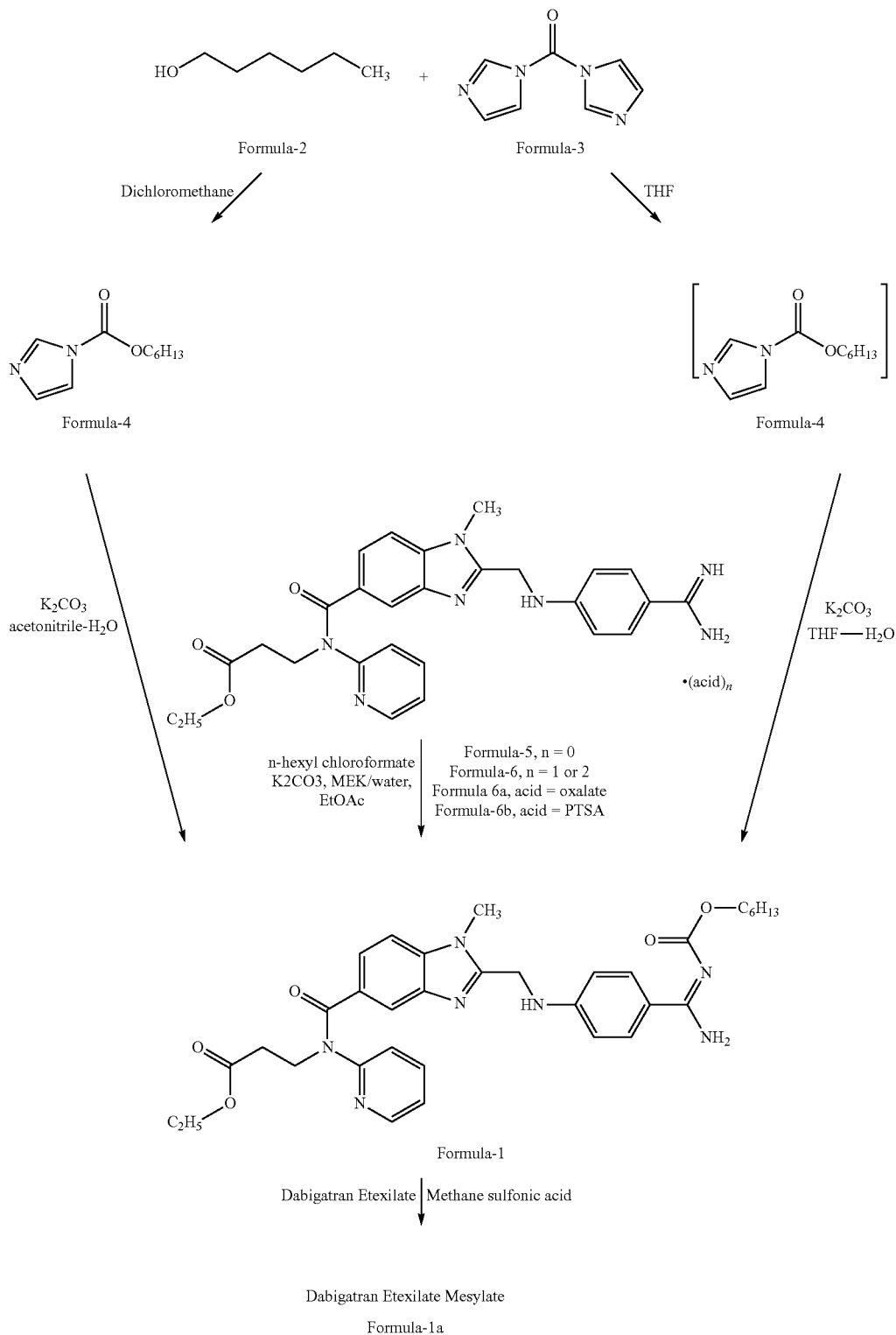

Scheme-2:
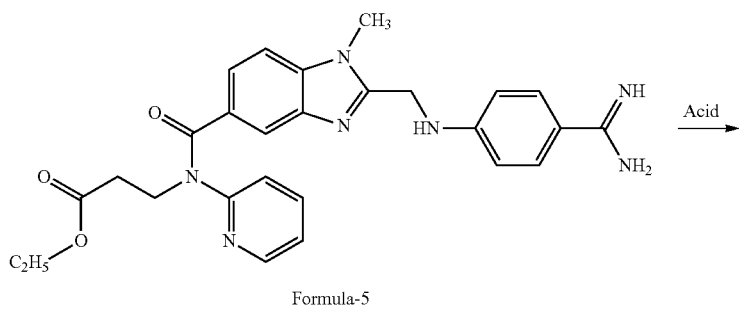
Formula-5
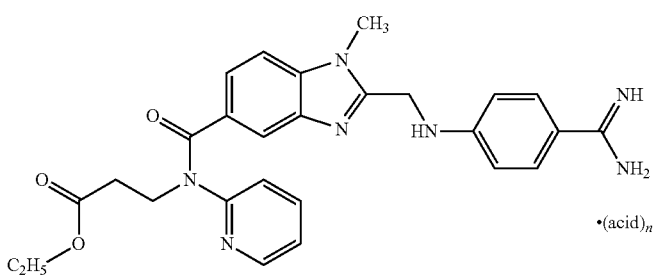
Formula-5, n = 0
Formula-6, n = 1 or 2
Formula-6a, acid = oxalic acid
Formula-6
Scheme-3:
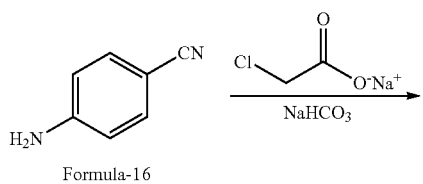
Formula-16
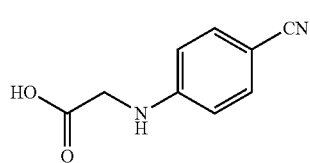
Formula-13
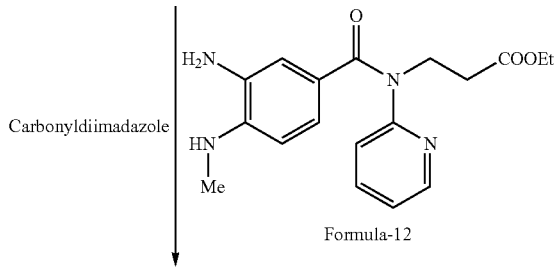
Formula-12
-continued
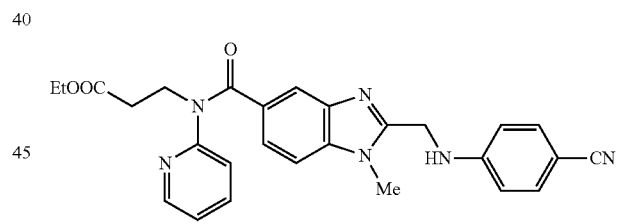
Formula-14
$\downarrow$ EtOH/HX
$(NH_4)_2CO_3$, $CaCl_2$
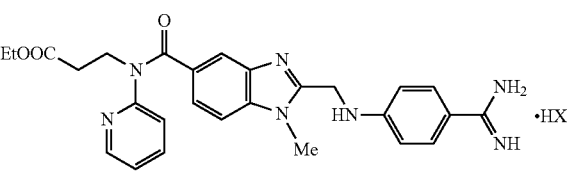
Formula-17
17a) X = Cl
Wherein X = halogen selected from Cl, Br or I
$\downarrow$ Base 27
-continued

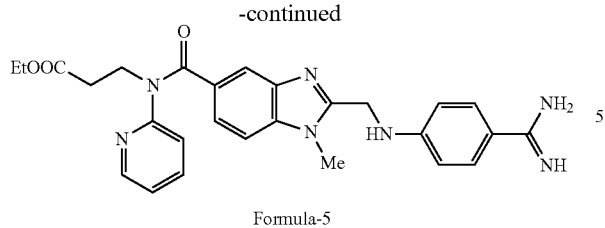

Formula-5

The compound of formula-12 can be prepared by the known methods which schematically represented as follows

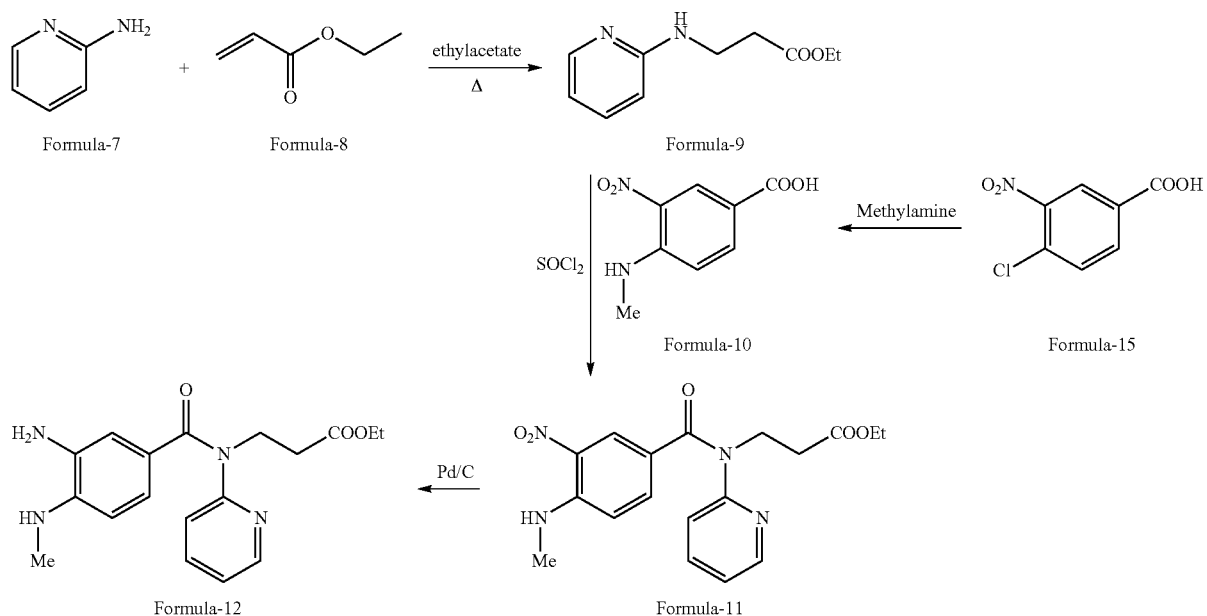

The process described in the present invention is demonstrated in examples illustrated below. These examples are provided as illustration only and therefore should not construed as limitation of the scope of the invention.

EXAMPLES

Example-1

Process for the Preparation of 1-methyl-2-[N-[4-amidinophenyl]aminomethyl]benzimidazol-5-yl-carboxylicacid-N-(2-pyridyl)-N-(2-ethoxy carbonylethyl)amide oxalate (Formula-6a)

A mixture of 1-methyl-2-[N-[4-amidinophenyl]aminomethyl]benzimidazol-5-yl-carboxylicacid-N-(2-pyridyl)-N-(2-ethoxycarbonylethyl)amide compound of formula-5 (100 g) and ethanol (1200 ml) was heated to 50-60° C. A solution of oxalic acid (25.25 g) in ethanol (1500 ml) was added to the above reaction mixture at 50-60° C. and stirred for 45 minutes. The reaction mixture was cooled to 25-35° C. and stirred for 6 hours at 25-35° C. Filtered the solid, washed with ethanol and then dried to get the title compound.

Yield: 140 g; Purity by HPLC: 99.11%

28

Example-2

Process for the Preparation of Dabigatran Etexilate (Formula-1)

A solution of 1-methyl-2[N-[4-amidinophenyl]aminomethyl]benzimidazol-5-yl-carboxylicacid-N-(2-pyridyl)-N-(2-ethoxycarbonylethyl)amide oxalate compound of formula-6a (100 g) in a mixture of acetonitrile (1200 ml) and water (800 ml) was cooled to 12-18° C. Potassium carbonate (66.24 g) was added to the above reaction mixture and stirred for 15 minutes at 12-18° C. n-hexyl chloroformate (28.95 g) was added to the reaction mixture and stirred for 4½ hours at 12-18° C. After completion of the reaction, the reaction mixture was quenched with water. Filtered the obtained solid, washed with acetonitrile and water. Dried the solid to get the title compound. Dichloromethane was added to the obtained compound and stirred for 15 minutes. Water was added to the reaction mixture and stirred for 20 minutes at 25-35° C. Both the organic and aqueous layers were separated, and the dichloromethane layer was washed with water followed by sodium chloride and then distilled off completely under reduced pressure. Acetone (600 ml) was added to the obtained residue and stirred for 45 minutes at 25-35° C. to obtain a clear solution. Water (500 ml) was added to the obtained solution and stirred for 45 minutes at 25-35° C. to get the solid. Filtered the solid, washed with water and finally with methyl tertiary butyl ether and then dried to get the pure title compound. Yield: 98 g; Purity by HPLC: 99.58%

Example-3

Process for the Preparation of Dabigatran Etexilate (Formula-4)

A solution of 1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-3a (100 g) in a mixture of methyl ethyl ketone (1200 ml)

and water (800 ml) was cooled to 12-18° C. Potassium carbonate (66.24 g) was added to the above reaction mixture and stirred for 15 minutes at 12-18° C. n-hexylchloroformate (28.95 g) was added to the reaction mixture and stirred for 4½ hours at 12-18° C. After completion of the reaction, the reaction mixture was quenched with water. Filtered the obtained solid, washed with methyl ethyl ketone and water. Dried the solid to get the title compound. Dichloromethane was added to the obtained compound and stirred for 15 minutes. Water was added to the reaction mixture and stirred for 20 minutes at 25-35° C. Both the organic and aqueous layers were separated, and the dichloromethane layer was washed with water followed by sodium chloride and then distilled off completely under reduced pressure. Acetone (600 ml) was added to the obtained residue and stirred for 45 minutes at 25-35° C. to obtain a clear solution. Water (500 ml) was added to the obtained solution and stirred for 45 minutes at 25-35° C. to get the solid. Filtered the solid, washed with water and finally with methyl tertiary butyl ether and then dried to get the pure title compound. Yield: 98 g; Purity by HPLC: 99.58%

Example-4

Purification of Dabigatran Etexilate (Formula-1)

A mixture of Dabigatran etexilate compound of formula-1 (100 g) and Ethyl acetate (600 ml) was heated to reflux temperature and then stirred for 2 hours at the same temperature. Filtered the reaction mixture through the hyflow bed. Washed the bed twice with hot ethyl acetate and ethanol (8 ml) was added to the obtained filtrate. The reaction mixture was further heated to reflux temperature and stirred for 1 hour at the same temperature. Cooled the reaction mixture to 25-35° C. and stirred for 3 hours. Filtered the solid, washed with ethyl acetate and then dried to get pure title compound.
Yield: 83 g; MP: 126-128° C.; Purity by HPLC: 99.58%
The melting point of Dabigatran etexilate obtained in this example is similar to the melting point of Dabigatran etexilate obtained in JMC, 2002, 45(9), 1757-1766.

Example-5

Process for the Preparation of Dabigatran Etexilate Mesylate (Formula-1a)

Figure 5:
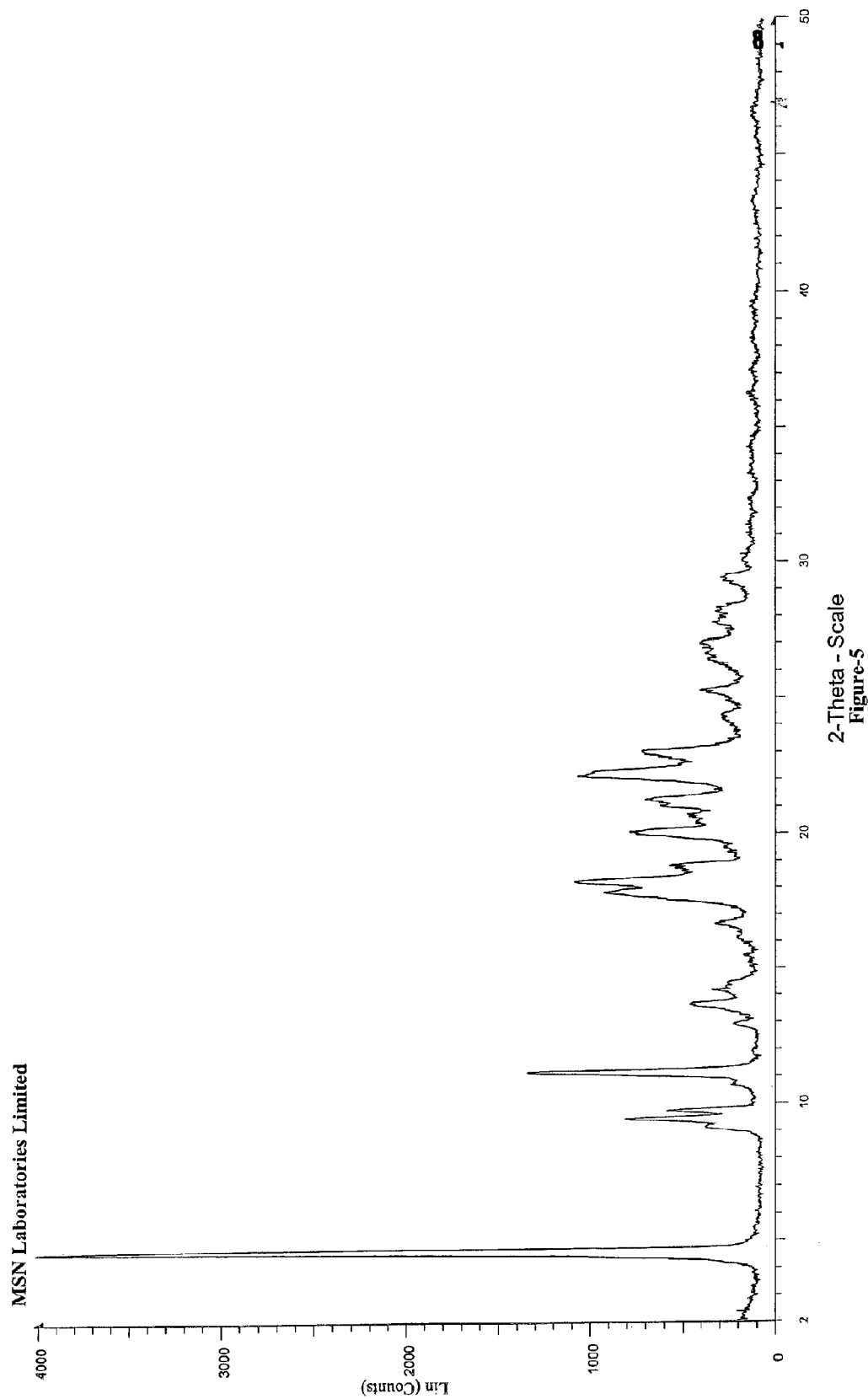

A solution of Dabigatran etexilate compound of formula-1 (100 g) in ethylacetate (600 ml) was heated to 40° C. and stirred for 45 minutes at 40° C. Filtered the reaction mixture through hyflow bed and cooled to 25-30° C. Ethanol (60 ml) was added to the filtrate at 25-35° C. A solution of methane sulfonic acid (15 g) in ethylacetate (1000 ml) was slowly added to the above reaction mixture over a period of 2 hours at 25-35° C. and stirred for 6 hours at the same temperature. Filtered the obtained solid, washed with ethyl acetate and then dried to get the title compound.
Yield: 105 g; Purity by HPLC: 99.64%
PXRD (FIG. 5) of Dabigatran etexilate mesylate obtained in this example is matches with the crystalline form-I of Dabigatran etexilate mesylate.

Example-6

Process the Preparation of 1-methyl-2-[N-[4-amidinophenyl]aminomethyl]benzimidazol-5-yl-carboxylicacid-N-(2-pyridyl)-N-(2-ethoxy carbonylethyl)amide (Formula-5)

Dissolved 1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-6a (100 g) in a mixture of acetonitrile (1200 ml) and water (800 ml) and cooled to 10-15° C. Potassium carbonate (66.24 g) was added to the reaction mixture and stirred for 60 minutes at 10-15° C. Filtered the obtained solid, washed with water and then dried to get title compound.
Yield: 80 g Example-7

Preparation of hexyl 1H-imidazole-1-carboxylate (Formula-4)

A solution of n-hexanol (25.95 g) in dichloromethane (400 ml) was slowly added to solution of N,N-carbonyldiimidazole (48.08 g) in dichloromethane (100 ml) and stirred for 2½ hour at 25-35° C. Water was added to the reaction mixture. Both the dichloromethane layer and aqueous layer were separated and the dichloromethane layer was distilled under reduced pressure to provide the title compound. Yield: 60 g Example-8

Preparation of Dabigatran Etexilate (Formula-1)

1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-6a (100 g) was added to acetonitrile (1200 ml) and water (800 ml) at 25-35° C. and then cooled to 12-18° C. Potassium carbonate (117 g) was added to the reaction mixture and stirred for 15 minutes at 12-18° C. A solution of hexyl 1H-imidazole-1-carboxylate compound of formula-4 (60 g) in acetonitrile (150 ml) was slowly added to the reaction mixture over a period of 25 minutes at 12-18° C. and stirred for 14 hours at 15-20° C. After completion of the reaction, water was added to the reaction mixture and stirred for 30 minutes. Filtered the solid, washed with acetonitrile followed by aqueous acetonitrile and then dried to get title compound. Dichloromethane was added to the obtained compound and stirred for 15 minutes. Water was added to the reaction mixture and stirred for 20 minutes at 25-35° C. Both the organic and aqueous layers were separated, and the dichloromethane layer was washed with water followed by sodium chloride and then distilled off completely under reduced pressure. Acetone (600 ml) was added to the obtained residue and stirred for 45 minutes at 25-35° C. to obtain a clear solution. Water (500 ml) was added to the obtained solution and stirred for 45 minutes at 25-35° C. to get the solid. Filtered the solid, washed with water and finally with methyl tertiary butyl ether and then dried to get the pure title compound. Further the obtained solid, recrystallized from ethylacetate and ethanol.
Yield: 95 g, M.P: 126-128° C. and Purity by HPLC: 99.58%

Example-9

Preparation of Dabigatran Etexilate (Formula-1)

1-methyl-2-[N-[4-amidinophenyl]aminomethyl]benzimidazol-5-yl-carboxylic acid-N-(2-pyridyl)-N-(2-ethoxycarbonylethyl)amide compound of formula-5 (100 g) was added to acetonitrile (1200 ml) and water (800 ml) at 25-35° C. and then cooled to 12-18° C. Potassium carbonate (138 g) was added to the reaction mixture and stirred for 15 minutes at 12-18° C. A solution of hexyl 1H-imidazole-1-carboxylate compound of formula-4 (66 g) in acetonitrile (150 ml) was slowly added to the reaction mixture over a period of 25 minutes at 12-18° C. and stirred for 14 hours at 15-20° C. After completion of the reaction, water was added to the reaction mixture and stirred for 30 minutes. Filtered the solid, washed with acetonitrile followed by aqueous acetonitrile and then dried to get title compound. Dichloromethane was added to the obtained compound and stirred for 15 minutes. Water was added to the reaction mixture and stirred for 20 minutes at 25-35° C. Both the organic and aqueous layers were separated, and the dichloromethane layer was washed with water followed by sodium chloride and then distilled off completely under reduced pressure. Acetone (600 ml) was added to the obtained residue and stirred for 45 minutes at 25-35° C. to obtain a clear solution. Water (500 ml) was added to the obtained solution and stirred for 45 minutes at 25-35° C. to get the solid. Filtered the solid, washed with water and finally with methyl tertiary butyl ether and then dried to get the pure title compound. Further the obtained solid recrystallized from ethylacetate and ethanol.

Yield: 114 g, M.P: 126-128° C. and Purity by HPLC: 90%

Example-10

Preparation of Dabigatran Etexilate (Formula-1)

A solution of n-hexanol (25.95 g) in tetrahydrofuran (400 ml) was slowly added to solution of N,N-carbonyldiimidazole (48.08 g) in tetrahydrofuran (100 ml) and stirred for 2½ hour at 25-35° C. to provide hexyl 1H-imidazole-1-carboxylate compound of formula-4. 1-methyl-2-[N-[4-amidinophenyl]aminomethyl]benzimidazol-5-yl-carboxylicacid-N-(2-pyridyl)-N-(2-ethoxycarbonylethyl)amide oxalate compound of formula-6a (100 g), tetrahydrofuran (700 ml), water (800 ml) and potassium carbonate (117 g) were added to the reaction mixture and stirred for 20 hours at 25-30° C. After completion of the reaction, filtered the solid, washed with tetrahydrofuran and then dried to get title compound. Dichloromethane was added to the obtained compound and stirred for 15 minutes. Water was added to the reaction mixture and stirred for 20 minutes at 25-35° C. Both the organic and aqueous layers were separated, and the dichloromethane layer was washed with water followed by sodium chloride and then distilled off completely under reduced pressure. Acetone (600 ml) was added to the obtained residue and stirred for 45 minutes at 25-35° C. to obtain a clear solution. Water (500 ml) was added to the obtained solution and stirred for 45 minutes at 25-35° C. to get the solid. Filtered the solid, washed with water and finally with methyl tertiary butyl ether and then dried to get the pure title compound. Further the obtained solid recrystallized from ethyl acetate and ethanol.

Yield: 100 g, Purity by HPLC: 99.58%.

Example-11

Preparation of Dabigatran Etexilate (Formula-1)

A solution of n-hexanol (30.6 g) in tetrahydrofuran (400 ml) was slowly added to solution of N,N-carbonyldiimidazole (55.08 g) in tetrahydrofuran (100 ml) and stirred for 2½ hour at 25-35° C. to provide hexyl 1H-imidazole-1-carboxylate compound of formula-4. 1-methyl-2-[N-[4-amidinophenyl]aminomethyl]benzimidazol-5-yl-carboxylicacid-N-(2-pyridyl)-N-(2-ethoxycarbonylethyl)amide compound of formula-5 (100 g), tetrahydrofuran (700 ml), water (800 ml) and potassium carbonate (138 g) were added to the reaction mixture and stirred for 20 hours at 25-30° C. After completion of the reaction, filtered the solid, washed with tetrahydrofuran and then dried to get title compound.

Yield: 115 g

Reference Example a) Preparation of Dabigatran Etexilate 55 g of 1-methyl-2-[N-[4-amidinophenyl]aminomethyl]benzimidazol-5-yl carboxylic acid-N-(2-pyridyl)-N-(2-ethoxycarbonylethyl)amide tosylate was dissolved in 437 ml of acetone and 273 ml of water. 16.4 g of hexyl chloroformate and 34 g of potassium carbonate was added to it at a temperature of about 15° C. After the end of the reaction, the precipitated product is filtered off and washed with acetone/water. Dissolved the obtained solid in 270 ml of acetone under heating and then filtered. The title product was crystallized by the addition of 220 ml of water. The isolated substance is dried under reduced pressure at 45° C.

Yield: 44 g b) Preparation of Dabigatran Etexilate Mesylate 100 g of 1-methyl-2-[N-[4-(N-n-hexyloxycarbonylamidino)phenyl]amino methyl]benzimidazol-5-yl-carboxylicacid-N-(2-pyridyl)-N-(2-ethoxycarbonylethyl) amide was dissolved in 890 ml of acetone under heating. A solution of 15 g of methane sulfonic acid in 200 ml of acetone was added to the reaction mixture. The solution is filtered and after the addition of 77 ml of acetone cooled to approximately 20° C. The precipitated product was filtered and washed with acetone then dried at 50° C. under reduced pressure.

Yield: 105 g

Purity by HPLC: 97.41%; Acid impurity: 1.04%; N-Oxide impurity: 1.16%; Impurity-X: 0.12%; Impurity-Y: 0.11%;

Example-12

Preparation of Dabigatran Etexilate Mesylate Compound of Formula-1a

Potassium carbonate (24.7 grams) was added to a solution of 1-methyl-2-[N-[4-amidinophenyl]aminomethyl]benzimidazol-5-ylcarboxylicacid-N-(2-pyridyl)-N-(2-ethoxycarbonylethyl) amide tosylate (40 grams) in acetone (318 ml) and water (198.5 ml) at 20-25° C. and stirred for 15 minutes. Cooled the reaction mixture to 5-10° C. and hexyl chloroformate (11.9 grams) was added to it then stirred for 30 minutes at 10-15° C. Filtered the precipitated product and washed with acetone/water mixture. The obtained solid was dissolved in approximately 180 ml of acetone and stirred the reaction mixture for 15 min at reflux temperature. Cooled the reaction mixture to 25-30° C. added water (175 ml) and stirred for 45 minutes. Filtered the precipitated solid and washed with acetone/water mixture. Acetone (267 ml) was added to the obtained solid and heated the reaction mixture to 50-55° C. Methanesulfonic acid (4.5 grams) in acetone (60 ml) was added to the reaction mixture at 50-55° C. The reaction mixture was subjected to carbon treatment and stirred for 30 minutes at 50-55° C. The reaction mixture was filtered through hyflow and the filtrate was cooled to 25-30° C. and stirred for 45 minutes. Filtered the precipitated solid and washed with acetone. The obtained dabigatran etexilate mesylate was dissolved in a mixture of acetone (245 ml) and methanol (70 ml) at 50-55° C. The reaction mixture was subjected to carbon treatment. The reaction mixture was cooled to 25-30° C. and stirred for 45 minutes. Cooled the reaction mixture to 0-5° C. and stirred for 45 minutes at the same temperature. Filtered the precipitated solid and washed with acetone and dried the material to get the highly pure title compound.

Yield: 28 g

Purity by HPLC: 99.84%; Acid impurity: Not detected; N-Oxide impurity: Not detected; Impurity-X: 0.01%; Impurity-Y: 0.01%.

Example-13

Purification of Dabigatran Etexilate Mesylate Compound of Formula-1a

A mixture of dabigatran etexilate mesylate (35 g) obtained as per reference example, acetone (245 ml) and methanol (70 ml) was heated to reflux temperature. Carbon (3.5 g) was added and stirred for 30 minutes. Filtered the reaction mixture through hyflow and the filtrate was cooled to 25-30° C. then stirred for 45 minutes. Further cooled the reaction mixture to 0-5° C. and stirred for 45 minutes at the same temperature. Filtered the precipitated solid and washed with acetone and then dried the material to get the highly pure title compound.

Yield: 27 g;

PXRD of dabigatran etexilate mesylate obtained as per this example is shown in the FIG. 4 and its DSC thermogram is shown in the FIG. 3.

Purity by HPLC: 99.90%; Acid impurity: Not detected; N-Oxide impurity: Not detected; Impurity-X: 0.01%; Impurity-Y: 0.01%.

Example-14

Purification of Dabigatran Etexilate Mesylate Compound of Formula-1a

A mixture of dabigatran etexilate mesylate (35 g) obtained as per reference example, acetone (245 ml) and ethanol (90 ml) was heated to reflux temperature. Carbon (3.5 g) was added and stirred for 30 minutes. Filtered the reaction mixture through hyflow and the filtrate was cooled to 25-30° C. then stirred for 45 minutes. Further cooled the reaction mixture to 0-5° C. and stirred for 45 minutes at the same temperature. Filtered the precipitated solid and washed with acetone and then dried the material to get the highly pure title compound.

Yield: 25 g; PXRD of dabigatran etexilate mesylate obtained as per this example is shown in the FIG. 4 and its DSC thermogram is shown in the FIG. 3.

Purity by HPLC: 99.83%; Acid impurity: 0.01%; N-Oxide impurity: 0.02%; Impurity-X: 0.03%; Impurity-Y: 0.02%.

Example-15

Purification of Dabigatran Etexilate Mesylate Compound of Formula-1a

Dabigatran etexilate mesylate (25 g) obtained as per reference example was dissolved in methanol (75 ml) at 25-30° C. Carbon (3.5 grams) was added and stirred for 30 minutes. Filtered the reaction mixture through hyflow. Acetone (200 ml) was added to the filtrate and stirred for 45 minutes. Filtered the precipitated solid and washed with acetone and then dried the material to get the highly pure title compound.

Yield: 17.1 g; PXRD of dabigatran etexilate mesylate obtained as per this example is shown in the FIG. 4 and its DSC thermogram is shown in the FIG. 3.

Purity by HPLC: 99.73%; Acid impurity: 0.01%; N-Oxide impurity: 0.015%; Impurity-X: 0.025%; Impurity-Y: 0.02%.

Example-16

Purification of Dabigatran Etexilate Mesylate Compound of Formula-1a

Dabigatran etexilate mesylate (25 g) obtained as per reference example was dissolved, in methanol (75 ml) at 25-30° C. Carbon (3.5 g) was added and stirred for 30 minutes. Filtered the reaction mixture through hyflow. Methylisobutylketone (200 ml) was added to the filtrate and stirred for 45 minutes. Filtered the precipitated solid and washed with methylisobutylketone and then dried the material to get the highly pure title compound.

Yield: 16.6 g.

Example-17

Purification of Dabigatran Etexilate Mesylate Compound of Formula-1a

Dabigatran etexilate mesylate (25 g) obtained as per reference example was dissolved in ethanol (95 ml) at 25-30° C. Carbon (3.5 g) was added and stirred for 30 minutes. Filtered the reaction mixture through hyflow bed. Ethyl acetate (200 ml) was added to the filtrate and stirred for 45 minutes. Filtered the precipitated solid and washed with acetone and then dried the material to get the highly pure title compound.

Yield: 17 g.

Example-18

Process for the Preparation of N-oxide Impurity

Hydrogen peroxide solution (50%) (20 ml) was added to a solution of 1-methyl-2-[N-[4-(N-n-hexyloxycarbonylamidino)phenyl]aminomethyl]benzimidazol-5-yl-carboxylicacid-N-(2-pyridyl)-N-(2-ethoxycarbonylethyl)amide (5 grams) in methanol (30 ml). The reaction mixture was stirred for 24 hours at 25-30° C. Quenched the reaction mixture with 10% aqueous sodium sulfite solution and stirred for 15 minutes. Methyl tertiary butyl ether was added to the reaction mixture and separated the both aqueous and organic layers. The solvent from the organic layer was evaporated to get the title compound.

Yield: 2.3 g; Mass m/z: 644

Example-19

Preparation of 2-(4-cyanophenylamino)acetic acid Compound of Formula-13

Sodium bicarbonate (21.35 g) was added to a mixture of 4-aminobenzonitrile compound of formula-12 (100 g) and water (1000 ml) followed by sodium 2-chloroacetate (197.42 g). Potassium iodide (5 g) followed by tertiary butyl ammonium bromide (2.5 g) were added to the reaction mixture. The reaction mixture was heated to the 90-95° C. and stirred for 24 hours at the same temperature. After completion of the reaction, the reaction mixture was cooled to 20-25° C. and $p^H$ was adjusted to 7.5 with ammonia. The reaction mixture was stirred for 20 minutes at 20-30° C. Filtered the reaction mixture and ethylacetate was added to the filtrate. The reaction mixture was stirred for 15 minutes. Both the ethylacetate and aqueous layers were separated and the $p^H$ of aqueous layer was adjusted to 2.5 using hydrochloric acid. The reaction mixture was stirred for 3 hours at 20-30° C. to precipitate the solid. Filtered the precipitated solid, water followed by hydrochloric acid were added to the obtained solid and stirred for 4 hours at 25-30° C. Filtered the solid, the obtained solid was slurried twice in water for 30-45 minutes and then dried to get the title compound. The same process can be repeated one more time to eliminates the impurities if present. Yield: 131 g Example-20

Preparation of 1-methyl-2-[N-(4-cyanophenyl)aminomethyl]benzimidazol-5-ylcarboxylicacid-N-(2-pyridyl)-N-(2-ethoxycarbonylethyl)amide Compound of Formula-14

A mixture of 2-(4-cyanophenylamino)acetic acid (139 g) and tetrahydrofuran (750 ml) was heated to 50-55° C. A solution of N,N'-carbonyldiimidazole (177.6 g) in tetrahydrofuran (1000 ml) was added to the above reaction mixture at the same temperature over a period of 1 hour and stirred for 2 hours at 50-55° C. A solution of ethyl 3-(3-amino-4-(methylamino)-N-(pyridin-2-yl)benzamido) propanoate compound of formula-12 (250 g) in tetrahydrofuran (1500 ml) was added over a period of 2 hours at 50-55° C. and heated to 60-65° C. The reaction mixture was stirred for 50 hours at 60-65° C. After completion of the reaction, distilled off the solvent from the reaction mixture. Acetic acid was added to the reaction mixture and heated to 95-100° C. The reaction mixture was stirred for 5 hours at 95-100° C. Distilled off the solvent completely under the reduced pressure and the reaction mixture was cooled to 25-30° C. Water was added to the reaction mixture and the product was extracted with dichloromethane. Dichloromethane layer was washed with water followed by sodium chloride. Distilled off the solvent completely from the dichloromethane layer to obtain title compound.

Yield: 300 g

Example-21

Preparation of 1-methyl-2-[N-[4-amidino phenyl] aminomethyl]benzimidazol-5-ylcarboxylicacid-N-(2-pyridyl)-N-(2-ethoxycarbonylethyl) amide Compound of Formula-5

Calcium chloride dihydrate (12.5 g) was added to a mixture of 1-methyl-2-[N-(4-cyanophenyl)aminomethyl]benzimidazol-5-ylcarboxylicacid-N-(2-pyridyl)-N-(2-ethoxycarbonylethyl) amide compound of formula-14 (50 g) and ethanol (750 ml) and stirred for 20 minutes. The reaction mixture was cooled to 0-5° C. and HCl gas was passed into the reaction mixture over a period of 5 hours at a temperature below 10° C. The temperature of the reaction mixture was raised to 25-30° C. and stirred for 8 hours at the same temperature. After completion of the reaction, the solvent was expelled out under $N_2$ pressure. The reaction mixture was cooled to 0-5° C. and slowly added ammonium formate (150 g). The reaction mixture was stirred for 30 minutes and ammonium carbonate (300 g) was added. The temperature of the reaction mixture was raised to 25-35° C. and stirred for 10 hours. After completion of the reaction, the reaction mixture was filtered and the filtrate was distilled under reduced pressure. A solution of 10% ethanol in ethyl acetate was added to the reaction mixture and stirred for 3 hours to obtain a solid. Filtered the obtained solid, washed with ethyl acetate and then dried to get the title compound. Yield: 45 g Example-22

Preparation of 2-(4-cyanophenylamino)acetic acid Compound of Formula-13

Sodium bicarbonate (21.35 g) was added to a mixture of 4-aminobenzonitrile compound of formula-16 (100 g) and water (1000 ml) followed by sodium 2-chloroacetate (197.42 g). Potassium iodide (5 g) followed by tertiary butyl ammonium bromide (2.5 g) were added to the reaction mixture. The reaction mixture was heated to the 90-95° C. and stirred for 24 hours at the same temperature. After completion of the reaction, the reaction mixture was cooled to 20-25° C. and pH was adjusted to 7.5 with ammonia. The reaction mixture was stirred for 20 minutes at 20-30° C. Filtered the reaction mixture and ethyl acetate was added to the filtrate. The reaction mixture was stirred for 15 minutes. Both the ethyl acetate and aqueous layers were separated and the $p^H$ of aqueous layer was adjusted to 2.5 using hydrochloric acid. The reaction mixture was stirred for 3 hours at 20-30° C. to precipitate the solid. Filtered the precipitated solid, water followed by hydrochloric acid were added to the reaction mixture and stirred for 4 hours at 25-30° C. Filtered the solid, water was added to it and stirred for 30-45 minutes. Filtered the solid, washed with water and then dried to get the title compound. The same process can be repeated another time to eliminates the impurities if present. Yield: 131 g Example-23

Preparation of 1-methyl-2-[N-(4-cyanophenyl)aminomethyl]benzimidazol-5-ylcarboxylicacid-N-(2-pyridyl)-N-(2-ethoxycarbonylethyl)amide Compound of Formula-14

A mixture of 2-(4-cyanophenylamino)acetic acid (139 g) and tetrahydrofuran (750 ml) was heated to 50-55° C. A solution of N,N'-carbonyldiimidazole (177.6 g) in tetrahydrofuran (1000 ml) was added to the above reaction mixture at the same temperature over a period of 1 hour and stirred for 2 hours at 50-55° C. A solution of ethyl 3-(3-amino-4-(methylamino)-N-(pyridin-2-yl)benzamido) propanoate compound of formula-12 (250 g) in tetrahydrofuran (1500 ml) was added over a period of 2 hours at 50-55° C. and heated to 60-65° C. The reaction mixture was stirred for 50 hours at 60-65° C. After completion of the reaction, distilled off the solvent from the reaction mixture. Acetic acid was added to the reaction mixture and heated to 95-100° C. The reaction mixture was stirred for 5 hours at 95-100° C. Distilled off the solvent completely under the reduced pressure and the reaction mixture was cooled to 25-30° C. Water was added to the reaction mixture and the product was extracted with dichloromethane. Both the dichloromethane and aqueous layers were separated and the dichloromethane layer was washed with water followed by sodium chloride. Distilled off the solvent completely from the dichloromethane layer to obtain title compound.

Yield: 300 g

Example-24

Preparation of 1-methyl-2-[N-[4-amidino phenyl] aminomethyl]benzimidazol-5-ylcarboxylicacid-N-(2-pyridyl)-N-(2-ethoxycarbonylethyl) amide hydrochloride Compound of Formula-17a Calcium chloride dihydrate (12.5 g) was added to a mixture of 1-methyl-2-[N-(4-cyanophenyl)aminomethyl]benzimidazol-5-ylcarboxylicacid-N-(2-pyridyl)-N-(2-ethoxy carbonyl ethyl)amide compound of formula-14 (50 g) and ethanol (750 ml) and stirred for 20 minutes. The reaction mixture was cooled to 0-5° C. and HCl gas was passed into the reaction mixture over a period of 5 hours at a temperature below 10° C. The temperature of the reaction mixture was raised to 25-30° C. and stirred for 8 hours at the same temperature. After completion of the reaction, the solvent was expelled out under N₂ pressure. The reaction mixture was cooled to 0-5° C. and slowly added ammonium formate (150 g). The reaction mixture was stirred for 30 minutes and ammonium carbonate (300 g) was added. The temperature of the reaction mixture was raised to 25-35° C. and stirred for 10 hours. After completion of the reaction, the reaction mixture was filtered and the filtrate was distilled under reduced pressure. A solution of 10% ethanol in ethyl acetate was added to the reaction mixture and stirred for 3 hours to obtain a solid. Filtered the obtained solid, washed with ethyl acetate and then dried to get the title compound. Yield: 45 g

We claim:

1. A process for preparing dabigatran etexilate compound of Formula-1

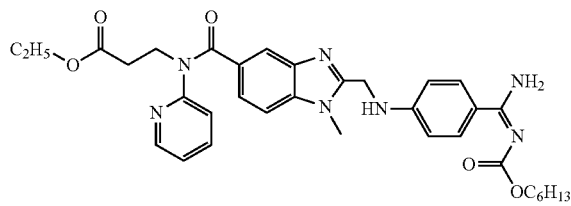

Formula-1 or a salt thereof, the process comprising:
a) reacting a compound of Formula-2

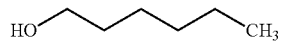

Formula-2 with a compound of Formula-3

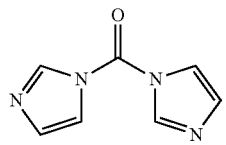

Formula-3 in a solvent selected from an ester solvent, an ether solvent, a hydrocarbon solvent, a polar aprotic solvent, a ketone solvent, an alcoholic solvent, a chloro solvent, a nitrile solvent or a nitro solvent, or a mixture thereof, to provide a compound of Formula-4,

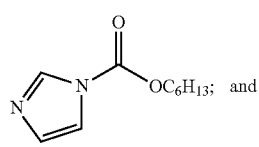

Formula-4 and b) reacting the compound of Formula-4 with a compound of Formula-5

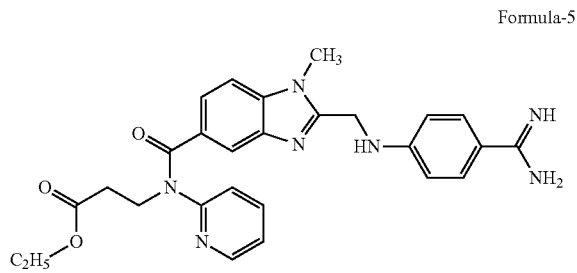 [SMILES: CCOC(=O)CCN(C(=O)c1ccc2c(c1)nc(CNc1ccc(C(=N)N)cc1)n2C)c1ccccn1]

Formula-5 or a compound of Formula-6

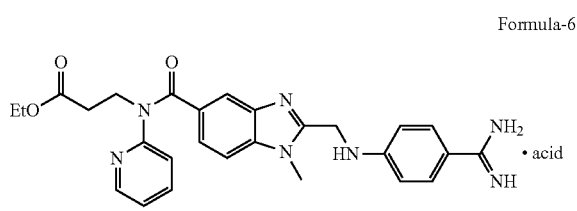 [SMILES: CCOC(=O)CCN(C(=O)c1ccc2c(c1)nc(CNc1ccc(C(=N)N)cc1)n2C)c1ccccn1]

Formula-6 in the presence of a base selected from an inorganic base or an organic base, or a mixture thereof, in a solvent selected from an ester solvent, an ether solvent, a hydrocarbon solvent, a polar aprotic solvent, a ketone solvent, an alcoholic solvent, a chloro solvent, a nitrile solvent or a nitro solvent, or a mixture thereof, to provide the compound of Formula-1.

2. The process according to claim 1, wherein
the solvent used in step (a) is a chloro solvent, ester solvent, ether solvent, ketone solvent or polar aprotic solvent; and
the solvent used in step (b) is ether solvent, ester solvent, ketone solvent, polar aprotic solvent or nitrile solvent; and
the base is an alkali metal carbonate or an alkali metal bicarbonate.

3. The process according to claim 1, wherein
the solvent used in step (a) is in an amount ranging from 2-10 volumes of solvent to 1 g of compound of Formula-5 or compound of Formula-6; and
the solvent used in step (b) is in an amount ranging from 5-50 volumes of solvent to 1 g of compound of Formula-5 or compound of Formula-6.

4. The process according to claim 1, wherein the mole proportions of base, compound of Formula-3 and compound of Formula-2 are in an amount ranging between 0.8-10, 0.8-6 and 0.8-6, respectively, per one mole of compound of Formula-5 or compound of Formula-6.

5. The process according to claim 1, wherein:
step (a) is performed in dichloromethane; and
step (b) is performed by reacting the compound of Formula-4 with the compound of Formula-5 or the compound of Formula-6a Formula-6a

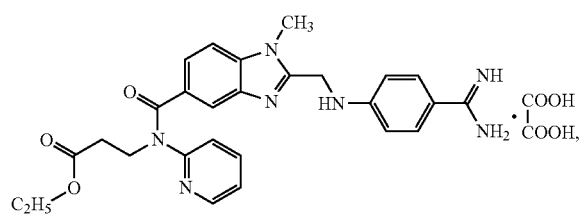

in the presence of potassium carbonate in aqueous acetonitrile to provide the compound of Formula-1.

6. The process according to claim 1, wherein the compound of Formula-4 is used in step (b) without isolation.

7. The process according to claim 1, further comprising:
a) treating the compound of Formula-5 with oxalic acid in ethanol to provide a compound of Formula-6a, Formula-6a and b) treating the compound of Formula-6a with potassium carbonate to provide the compound of Formula-5 and isolating the compound of Formula-5 to provide pure compound of Formula-5.

8. The process according to claim 1, further comprising:
a) reacting a compound of Formula-16

Formula-16 with sodium 2-chloroacetate in presence of a base selected from alkali metal hydroxides, alkali metal carbonates or alkali metal bicarbonates in presence of tertiary butyl ammonium bromide in a solvent selected from alcohol solvents, ketone solvents, polar solvents or mixtures thereof to provide a compound of Formula-13, Formula-13 b) condensing the compound of Formula-13 with a compound of Formula-12

Formula-12 in the presence of carbonyldiimidazole in a suitable solvent selected from ether solvents, hydrocarbon solvents, ester solvents, ketone solvents or mixtures thereof to provide a compound of Formula-14, Formula-14 c) reacting the compound of Formula-14 with ammonium carbonate in presence of a Lewis acid selected from aluminium chloride(AlCl₃), aluminium bromide (AlBr₃), boron trichloride (BCl₃), boron trifluoride (BF₃), Iron(III) chloride(FeCl₃), Tin(IV) chloride (SnCl₄), calcium chloride dihydrate (CaCl₂.2H₂O), or calcium chloride (CaCl₂), and in presence of hydrochloride gas in a solvent selected from alcohol solvents, ether solvents, ketone solvents or mixtures thereof, to provide a compound of Formula-17a, Formula-17a d) converting the compound of Formula-17a into compound of Formula-5 by treating the compound of Formula-17a with a base selected from alkali metal hydroxides, alkali metal carbonates or alkali metal bicarbonates or triethylamine, isopropyl ethylamine, diisopropyl amine, diisopropyl ethylamine, N-methyl morpholine, piperidine or pyridine in a solvent selected from alcohol solvents, ether solvents, ketone solvents, ester solvents, hydrocarbon solvents, chloro solvents, polar solvents or mixtures thereof.

9. The process according to claim 1, wherein the acid in the compound of Formula-6 is oxalic acid, 2,5-dihydroxy benzoic acid, benzene sulfonic acid, cyclamic acid, ethanedisulfonic acid, ethane sulfonic acid, D-glucaronoic acid, glycolic acid, mandelic acid, palmitic acid, oleic acid, stearic acid, cinnamic acid, camphor sulfonic acid, adipic acid, naphthalene-2-sulfonic acid or naphthalene-1,5-disulfonic acid.

10. The process according to claim 9, wherein the compound of Formula-6 is represented by a compound of Formula-6a,

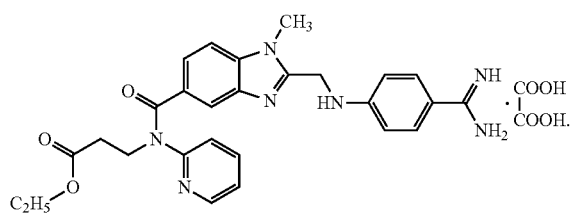

Formula-6a

11. The process according to claim 10, wherein the compound of Formula-6a is a crystalline solid herein designated as crystalline form-M and is characterized by:

a) its powder XRD pattern having peaks at about 7.6, 11.7, 14.5, 18.0, 18.2, 22.8, 24.8 and 25.3±0.2 degrees of two-theta; or b) its DSC thermogram showing endotherm at about 203.53° C.

12. The process according to claim 10, further comprising:

a) treating a compound of Formula-5 with an acid in a solvent selected from alcohol solvents, chloro solvents, ether solvents, nitro solvents, ketone solvents, ester solvents, nitrile solvents or hydrocarbon solvents and;

b) isolating the solid obtained in step (a) to provide the compound of Formula-6.

13. The process according to claim 1, wherein the compound of Formula-1 is dabigatran etexilate mesylate and is characterized by:

a) having a purity greater than 99.50% by HPLC; or b) having a purity greater than 99.75% by HPLC; or c) having a purity greater than 99.95% by HPLC; or d) containing less than 0.05% of Impurity-X and Impurity-Y by HPLC; or e) containing less than 0.01% of Impurity X and Impurity Y by HPLC; or f) containing less than 0.1% by HPLC of an acid impurity represented by the following structural formula:

and an N-oxide impurity represented by the following structural formula:

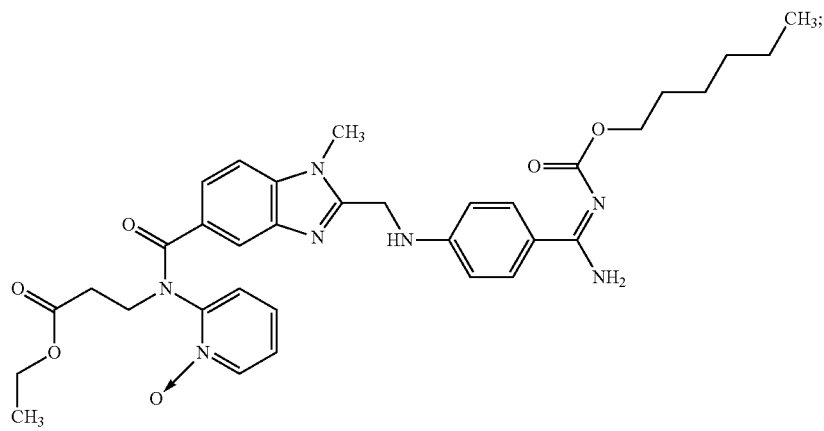 [SMILES: CCCCCCOC(=O)/N=C(/N)c1ccc(NCc2nc3cc(C(=O)N(CCC(=O)OCC)c4ccccn4)ccc3n2C)cc1 ; O]

Or
  g) containing less than 0.05% by HPLC of the acid impurity and the N-oxide impurity; or
  h) containing less than 0.01% by HPLC of the acid impurity and the N-oxide impurity.

14. The process according to claim 5, wherein the compound of Formula-4 is used in step (b) without isolation.

15. The process according to claim 5, further comprising:
  a) treating the compound of Formula-5 with oxalic acid in ethanol to provide compound of Formula-6a, Formula-6

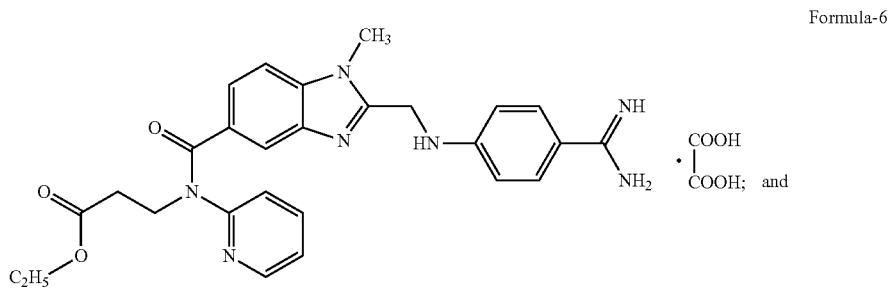 [SMILES: CCOC(=O)CCN(C(=O)c1ccc2c(c1)nc(CNc1ccc(C(=N)N)cc1)n2C)c1ccccn1 ; O=C(O)C(=O)O]

b) treating the compound of Formula-6a with potassium carbonate to provide the compound of Formula-5 and isolating the compound of Formula-5 to provide pure compound of Formula-5.

16. The process according to claim 2, wherein:

in step (a), the chloro solvent is dichloromethane, chloroform or dichloroethane; the ester solvent is ethyl acetate, methyl acetate or isopropyl acetate; the ether solvent is tetrahydrofuran, diethyl ether or methyl tert-butyl ether; the ketone solvent is acetone, methylethylketone, propanone or methylisobutylketone; and the polar aprotic solvent is dimethylformamide or acetonitrile; and in step (b), the ether solvent is tetrahydrofuran, methyl tert-butyl ether or diethyl ether; the ester solvent is methyl acetate, ethyl acetate or isopropyl acetate; the ketone solvent is acetone, propanone, methyl ethyl ketone or methylisobutylketone; the polar aprotic solvent is dimethylformamide or dimethylacetamide; and the nitrile solvent is acetonitrile, propionitrile or its mixtures with water.

* * * * *

UNITED STATES PATENT AND TRADEMARK OFFICE
CERTIFICATE OF CORRECTION

PATENT NO. : 9,006,448 B2
APPLICATION NO. : 13/995786
DATED : April 14, 2015
INVENTOR(S) : Reddy et al.

Page 1 of 1

It is certified that error appears in the above-identified patent and that said Letters Patent is hereby corrected as shown below:

In the Claims:

In Column 44, Claim 15, line 33, delete "Formula-6" and insert --Formula-6a--.

Signed and Sealed this
Twentieth Day of October, 2015

Michelle K. Lee
*Director of the United States Patent and Trademark Office*